United States Patent
Foster et al.

(10) Patent No.: US 6,258,341 B1
(45) Date of Patent: *Jul. 10, 2001

(54) STABLE GLASSY STATE POWDER FORMULATIONS

(75) Inventors: Linda C. Foster, Mountain View; Mei-chang Kuo, Palo Alto; Sheila R. Billingsley, Sunnyvale, all of CA (US)

(73) Assignee: Inhale Therapeutic Systems, Inc., San Carlos, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/733,225

(22) Filed: Oct. 17, 1996

Related U.S. Application Data

(63) Continuation of application No. PCT/US96/05070, filed on Apr. 12, 1996, which is a continuation of application No. 08/423,515, filed on Apr. 14, 1995.

(51) Int. Cl.[7] .................................................. A61K 9/12
(52) U.S. Cl. ........................ 424/45; 424/484; 424/486; 424/488; 424/489; 128/203.15
(58) Field of Search .................................. 424/489, 488, 424/490, 486, 484, 45; 514/54; 128/203.15

(56) References Cited

U.S. PATENT DOCUMENTS

| | | |
|---|---|---|
| 4,818,542 | 4/1989 | DeLuca et al. . |
| 4,891,319 | 1/1990 | Roser . |
| 5,057,392 | 10/1991 | McCabe et al. . |
| 5,098,893 | * 3/1992 | Franks ................................... 514/54 |
| 5,098,955 | 3/1992 | Pettit, Jr. . |
| 5,200,399 | 4/1993 | Wettlaufer et al. .................... 514/23 |
| 5,290,765 | 3/1994 | Wettlaufer et al. .................... 514/23 |

FOREIGN PATENT DOCUMENTS

| | | |
|---|---|---|
| 0524748 A1 | * 6/1992 | (EP) . |
| 0 520 748 A1 | 12/1992 | (EP) . |
| WO 95/05805 | 3/1995 | (WO) . |

(List continued on next page.)

OTHER PUBLICATIONS

Angell, (1995) "Formation of Glasses from Liquids and Biopolymers," *Science* 267:1924–1935.
Clark, et al., (1996) "The Balance Between Biochemical and Physical Stability For Inhalation Protein Powders: rhDNASE As An Example," *Respiratory Drug Delivery V* 167–174.

(List continued on next page.)

*Primary Examiner*—Thurman K. Page
*Assistant Examiner*—B. Fubara
(74) *Attorney, Agent, or Firm*—Susan T. Evans; Felissa H. Cagan; Stephen L. Hurst

(57) ABSTRACT

A powdered, dispersible composition having stable dispersibility over time is provided. The composition exhibits a characteristic glass transition temperature ($T_g$) and a recommended storage temperature ($T_s$), wherein the difference between $T_g$ and $T_s$ is at least about 10° C. (i.e. $T_g-T_s$ is greater than 10° C.). The composition comprises a mixture of a pharmaceutically-acceptable glassy matrix and at least one pharmacologically active material within the glassy matrix. It may be further mixed with a powdered, pharmaceutically-acceptable carrier.

It is particularly valuable in unit dosage from having a moisture barrier, in combination with appropriate labelling instructions.

A process for producing a powdered dispersible composition is also provided, wherein the process comprises removing the solvent from a solution comprising a solvent, a glass former and a pharmacologically active material under conditions sufficient to form a glassy matrix having the pharmacologically active material within the matrix.

32 Claims, 10 Drawing Sheets

FOREIGN PATENT DOCUMENTS

| | | | |
|---|---|---|---|
| WO 96/33744 | 10/1996 | (WO) | . |
| WO 97/41031 | 11/1997 | (WO) | B65B/1/04 |
| WO 97/41833 | 11/1997 | (WO) | A61K/9/12 |

OTHER PUBLICATIONS

Fäldt and Bergenstahl, (1994) "The Surface Composition of Spray–Dried Protein–Lactose Powders," *Colloids and Surfaces A: Physiochemical and Engineering Aspects* 90:183–190.

Fox, (1995) "Putting Proteins Under Glass," *Science* 267:1922–1923.

Franks, (1993) "Solid Aqueous Solutions," *Pure & Appl. Chem.* 65:2527–2537.

Franks, et al. (1992) "Materials Science and the Production of Shelf–Stable Biologicals," *Pharmaceutical Technology* 32–50.

Franks, (1989) "SEPARATION, Improved Freeze–Drying, An Analysis of the Basic Scientific Principles," *Process Biochemistry* 24:R3–R7.

Franks and Murase, (1992) "Nucleation and Crystallization In Aqueous Systems During Drying: Theory and Practice," *Pure & Appl. Chem.* 64:1667–1672.

Gibbs and DiMarzio, (1958) "Nature of the Glass Transition and the Glassy State," *The Journal of Chemical Physics* 28:373–383.

Roos and Karel, (1990) "Differential Scanning Calorimetry Study of Phase Transitions Affecting the Quality of Dehydrated Materials," *Biotechnol. Prog.* 6:159–163.

Slade and Levine, (1988) "Non–equilibrium Behavior of Small Carbohydrate–Water Systems," *Pure & Appl. Chem.* 60:1841–1864.

Wolanczyk, (1989) "Differential Scanning Calorimetry Analysis of Glass Transitions," *Cryo–Letters* 10:73–76.

\* cited by examiner

Moisture sorption/desorption isotherm for I-004 formulations at 25°C

X-ray diffraction pattern for I-004 formulation. The absence of sharp peaks in this pattern shows that this sample was amorphous.

STABLE GLASSY STATE POWDER FORMULATIONS

CROSS REFERENCE TO RELATED APPLICATIONS

This application is a continuation-in-part of PCT Application No. PCT/US 96/05070, filed Apr. 12, 1996, which is a continuation-in-part of U.S. Ser. No. 08/423,515, filed Apr. 14, 1995, which applications are incorporated herein by reference in their entirety.

BACKGROUND

1. Field of the Invention

This invention relates to powdered pharmaceutical compositions that exhibit improved stability of dispersibility over time for inhalation therapy, to processes for preparing such compositions, and to methods for treating certain disease states using such compositions. The invention is based on the discovery that the dispersibility of a powdered pharmaceutical composition can be maintained over time if the composition is prepared in a glassy state. While it has been known that the chemical stability of a pharmaceutical may be maintained in the glassy state, this is the first recognition that a glassy state composition may be used to maintain dispersibility of a powdered composition over time.

2. Background of the Invention

Over the years, certain drugs have been sold in compositions suitable for forming a drug dispersion for oral inhalation and consequent pulmonary absorption to treat various conditions in humans. Such pulmonary drug delivery compositions are designed to be delivered by inhalation of a drug dispersion by the patient so that the active drug within the dispersion can reach the lung. It has been found that certain drugs delivered to the lung are readily absorbed through the alveolar region directly into blood circulation. Thus, pulmonary delivery can be effective both for systemic delivery to treat various diseases and for localized delivery to treat diseases of the lungs.

Several approaches are used to deliver drugs via pulmonary absorption. These include liquid nebulizers, propellant-based metered dose inhalers (MDI's), and breath-actuated or air-assisted dry powder inhalers (DPI's). Aerosol dry powder inhalers provide a particularly promising approach for pulmonary delivery of drugs. DPI's usually contain the powdered drug in a desiccated reservoir or blister pack. Inhaled or compressed air disperses the powder out of the device either directly into the patient's mouth (breath-actuated DPI) or into a holding chamber (air assisted DPI). (See e.g. U.S. patent application Ser. No. 08/423,568, filed Apr. 14, 1995, which is incorporated herein by reference). Propellant based MDIs may also employ a dry powdered drug which is suspended in a liquified gas propellant. To deliver the drug, the pressurized gas is abruptly released through a valve and in the resulting spray, the propellant evaporates almost immediately leaving a fine dry powder. Aerosol powders are useful for the delivery of various pharmaceutical products including small molecules, such as steroids; peptides, such as hormone agonists; and proteins, such as insulin.

However, various disadvantages are evident with dry powder aerosol systems. If powder particles agglomerate to each other or adhere to the container or package walls over time, the concentration and thus the dosage of the delivered product will change. Furthermore, the powder particles may agglomerate and form hard cakes. With propellant systems, valve clogging may occur if the powder agglomerates or the powder concentration is too high. Additionally, powder may deposit on the value seat and prevent the valve from closing properly. This leads to leakage of the propellant. Agglomeration also reduces the amount of drug that can be deposited in the lung, since particles typically must be below about 5 $\mu$m for deposition in the respiratory bronchioles and below about 2 $\mu$m for deposition through the alveolar ducts and alveoli. As an aerosol dry powder is stored on the shelf longer, agglomeration may become more pronounced. The accumulation of moisture in particular can accelerate the rate of agglomeration. This degradation of solid state stability of the formulation over time makes it difficult to ensure delivery of a consistent and accurate dose of the drug active during the shelf life of the compound. With aerosol powders, shelf life is dependent on both the chemical stability of the active drug and the physical stability of the solid state delivery system. When the active drug is a small molecule, such as a steroid, it typically has good chemical stability, thus shelf life is dictated more by the physical stability of the dosage form. When the active is a labile protein, such as $\alpha$-1 antitrypsin, the shelf life is dictated by both the chemical stability of the active drug in the dosage form and the physical stability of the dosage form itself. This has made the development of delivery systems for oral inhalation delivery of labile peptides and proteins particularly difficult. Additionally, since proteins and other macromolecules are poorly absorbed via other non-invasive routes of administration, pulmonary absorption is generally preferred.

The poor chemical stability of proteins in aqueous dosage forms is well known and solid dosage forms for proteins, i.e. dried proteins, are generally preferred. However, even in solid dosage forms, some proteins can be relatively unstable. This poor stability can be a product of both the method of preparing solid dosage forms, where the active drug is a protein, and of the storage environment around the protein within the dosage form.

A common method used to prepare relatively stable dry powders containing proteins is lyophilization (freeze-drying). However, lyophilization and further processing can force a protein to undergo significant chemical and physical changes. Such changes result in a loss of activity of the protein as a result of various forces including concentration of salts, precipitation/crystallization reactions, shear, pH, amount of residual moisture remaining after freeze-drying, and the like. This loss is effectuated in part by physical changes to the tertiary structure of the protein, i.e. by unfolding.

Numerous solutions to the problem of protein stability in the dried form have been proposed in the literature. To optimize protein stability during lyophilization (process stability), for instance, the use of pH specific stabilizing ligands and non-specific stabilizing additives has been suggested. To stabilize a protein after lyophilization, it has been suggested that the excipients form an amorphous glass with the protein. By supercooling a solution comprising a protein and excipients, freezing, wherein crystal habits can form, is bypassed and the solution forms a syrup followed by a viscoelastic rubber, and finally a glassy substance. The result is an amorphous solid, wherein the glassy excipient material, e.g. sucrose, is in an amorphous glassy form and encases the protein, thereby preventing any unfolding and slowing any molecular interactions or crossreactivity to a point of essential nonexistence, due to greatly reduced mobility of the protein and other molecules within the glassy composition.

This process has been postulated to occur either via mechanical immobilization of the protein by the amorphous glass or via hydrogen bonding to polar and charged groups on the protein, i.e. via water replacement, thereby preventing drying induced denaturation and inhibiting further degradative interactions. As long as the glassy solid is at a temperature below its glass transition temperature and the residual moisture remaining in the excipients is relatively low, the labile protein can remain relatively stable.

However, maintaining chemical and biological activity of the active protein is only half of the challenge where the delivery system comprises a dry powder aerosol dosage form. As previously discussed, the solid state stability of the dosage form itself must be maintained. That is, the dispersibility over time of the aerosol powder must be maintained. The importance of consistent physical stability of the aerosol powder dosage form is made evident by the need to accurately deliver relatively low doses of highly active proteins and peptides that are efficacious within very narrow therapeutic ranges. The high cost of many proteins and peptides also makes it critical to ensure that a substantial portion of available active drug dispersed within a dosage form is delivered to the pulmonary epithelia. Furthermore, for proteins, peptides, and small molecule pharmaceutical formulation for pulmonary delivery via oral inhalation, the U.S. Food and Drug Administration (FDA) requires that a given drug delivery system deliver the active drug at a concentration consistently within 85–115% of the labeled dose for the active, i.e. a delivered dose ±15% of the labeled dose. While the prior art has at least in part addressed the problems of chemical and physical stability of active protein drugs, it has not adequately addressed the issue of solid state stability of an aerosol dry powder, i.e. dispersibility, for delivering proteins. Nor has the prior art addressed the solid state stability of amorphous dry powder inhalable formulations comprising small molecules or peptides.

Thus, there is a need for a means to deliver drugs via pulmonary absorption that ensures physical stability of the solid state dosage form over time. That is, there is a need for an aerosol dry powder dosage form or similar dosage form that has a stable dispersibility over time.

3. Objects of the Invention

It is an object of this invention to provide a pharmaceutical composition, particularly in a unit dosage form, for pulmonary administration that has stable dispersibility over time.

It is a further object of this invention to provide a process for manufacturing a pharmaceutical composition for pulmonary administration that has stable dispersibility over time.

A still further object of this invention is to provide a process for administering a pharmaceutical composition for pulmonary administration that has stable dispersibility over time.

A still further object of this invention is to provide a novel drug delivery system that is capable of maintaining a stable level of dispersibility over time.

SUMMARY OF THE INVENTION

One aspect of this invention is a powdered, dispersible composition having stable dispersibility over time, a characteristic glass transition temperature ($T_g$) and a recommended storage temperature ($T_s$), wherein the difference between $T_g$ and $T_s$ is at least about 10° C. (i.e. $T_g-T_s$ is greater than 10° C.), which composition comprises a mixture of a pharmaceutically-acceptable glassy matrix and at least one pharmacologically active material within the glassy matrix.

Another aspect of this invention is a powdered dispersible composition in unit dosage form having stable dispersibility over time and a characteristic glass transition temperature ($T_g$), in combination with labelling instructions for treating pulmonary or systemic disease in a mammalian subject that include a recommended storage temperature ($T_s$), wherein the difference between $T_g$ and $T_s$ is at least about 10° C. The composition comprises a pharmaceutically acceptable glassy matrix and at least one pharmaceutically active material within the amorphous glassy matrix.

Still another aspect of this invention is a process for producing a powdered dispersible composition having stable dispersibility over time, a characteristic glass transition temperature ($T_g$) and a recommended storage temperature ($T_s$) wherein the difference between $T_g$ and $T_s$ is at least about 10° C. The process comprises removing the solvent from a solution comprising a solvent, a glass former and a pharmacologically active material under conditions sufficient to form a glassy matrix having the pharmacologically active material within the matrix.

DETAILED DESCRIPTION OF PRESENTLY PREFERRED EMBODIMENTS

Definitions

Figure 1A:
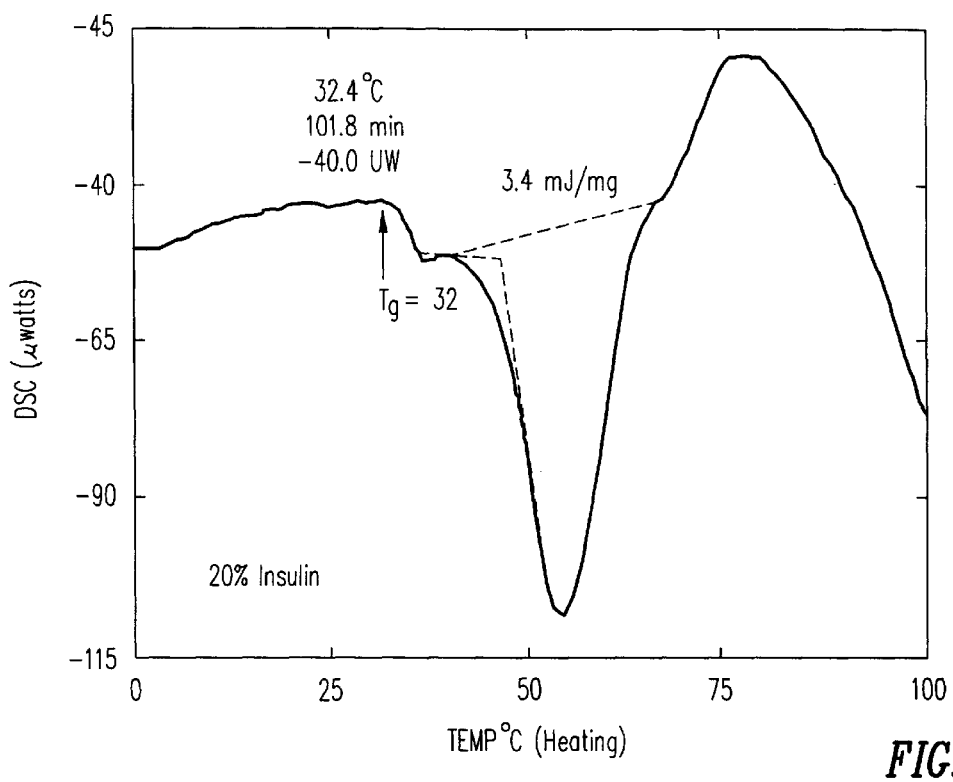
FIG. 1A is a DSC (differential scanning calorimetry) thermogram of an initial formulation of Example 1.

The following definitions of terms are provided to help interpret the scope and breadth of the appended claims.

Delivered Dose

The phrase "delivered dose" as used herein refers to the percentage of the drug in a pharmaceutical dosage form employing an aerosol based delivery system that is delivered from the mouthpiece of the device. For example, a delivered dose of 70% indicates that 70% of the total amount of drug in the dosage form was delivered from the mouthpiece of the device.

The term "dispersibility" means the degree to which a powder composition can be dispersed (i.e. suspended or aerosolized) in a current of air so that the dispersed particles can be respired or inhaled into the lungs of a subject. For example, a powder composition that is only 10% dispersible means that only 10% of the mass of finely-divided particles making up the composition can be suspended for oral inhalation into the lungs; 50% dispersibility means that 50% of the mass can be suspended. A standard measurement of dispersibility is described hereinafter.

Glass

The term "glass" or "glassy state" or "glassy matrix," as used herein, refers to a liquid that has lost its ability to flow, i.e. it is a liquid with a very high viscosity, wherein the viscosity ranges from $10^{10}$ to $10^{14}$ pascal-seconds. It can be viewed as a metastable amorphous system in which the molecules have vibrational motion but have very slow (almost immeasurable by today's techniques) rotational and translational components. As a metastable system, it is stable for long periods of time when stored well below the glass transition temperature. Because glasses are not in a state of thermodynamic equilibrium, glasses stored at temperatures at or near the glass transition temperature relax to equilibrium upon storage and lose their high viscosity. The resultant rubbery or syrupy, flowing liquid can lead to physical instability of the product. While a glass can be obtained by many different routes, it appears to be fundamentally the same material by whatever route it was taken. The process used to obtain a glassy matrix for the purposes of this invention is generally a solvent evaporation technique.

Glass Transition Temperature

The glass transition temperature is represented by mil the symbol $T_g$ and is the temperature at which a composition changes from a glassy or vitreous state to a syrup or rubbery state. Generally $T_g$ is determined using differential scanning calorimetry (DSC) and is standardly taken as the temperature at which onset of the change of heat capacity (Cp) of the composition occurs upon scanning through the transition. The definition of $T_g$ is always arbitrary and there is no present international convention. The $T_g$ can be defined as the onset, midpoint or endpoint of the transition; for purposes of this invention we will use the onset of the changes in Cp when using DSC and DER. See the article entitled "Formation of Glasses from Liquids and Biopolymers" by C. A. Angell: Science, 267, 1924–1935 (Mar. 31, 1995) and the article entitled "Differential Scanning Calorimetry Analysis of Glass Transitions" by Jan P. Wolanczyk: Cryo-Letters, 10, 73–76 (1989). For detailed mathematical treatment see "Nature of the Glass Transition and the Glassy State" by Gibbs and DiMarzio: Journal of Chemical Physics, 28, NO. 3, 373–383 (March, 1958). These articles are incorporated herein by reference.

MMAD

The abbreviation "MMAD" means mass median aerodynamic diameter. It refers to the particle size distribution of the particles of a dispersible powder when they are dispersed as an aerosol. The determination is generally made using a cascade impactor. For a discussion see Remington's Pharmaceutical Sciences, 18th Edition at pp. 1620–22.

MMD

The abbreviation MMD means mass median diameter. It refers to the particle size distribution of the bulk powder, as generally measured by centrifugal sedimentation techniques (e.g. The Horiba Particle Size Analyzer—Model CAPA700 is useful).

Powder

The term "powder" as used herein refers to a composition that consists of finely dispersed solid particles that are substantially free flowing and capable of being readily dispersed in an inhalation device and subsequently inhaled by a subject so that the particles reach the lungs to permit penetration into the alveoli.

Recommended Storage Temperature

As used herein, the "recommended storage temperature" for a composition is the temperature ($T_s$) at which a powdered drug composition is to be stored to maintain the activity of the drug over the shelf life of the composition. This temperature is initially determined by the manufacturer of the composition and approved by the governmental agency responsible for approval of the composition for marketing (e.g. the Food and Drug Administration [FDA] in the U.S.). This temperature will vary for each approved drug product depending on the temperature sensitivity of the active drug and other materials in the product. The recommended storage temperature will vary from about 0° to about 40° C., but generally will be ambient temperature, i.e. about 25° C. Usually a drug product will be kept at a temperature that is at or below the recommended storage temperature.

Composition of the Invention

As discussed previously, it is difficult to ensure consistent dispersibility over time, i.e. solid state stability, of dispersible powders. Inconsistent dispersibility of an aerosol powder over time leads to a number of undesirable consequences including inconsistent dosing of the active drug and inconsistent and insufficient delivery of a therapeutically effective amount of active drug. Thus, a dispersible powder that has stable dispersibility over time is highly desirable.

The present invention is based, at least in part, on the unexpected discovery that the dispersibility of a pharmaceutical powder for pulmonary administration can be maintained over time if the powder dosage form is prepared in a glassy state and the difference between the $T_g$ and the $T_s$ of the composition is greater than about 10° C. and preferably exceeds about 20° C. While not intending to be limited to a particular theory, it is believed that this phenomenon may in part be a result of the convoluted surfaces of powder particles that result when the particles are in an amorphous glassy state. This glassy surface appears to reduce the probability that individual particles will agglomerate with each other when stored over time. A particularly preferred embodiment of the present invention is one where at least the outermost regions, including the outer surface, of the powder particles are in an amorphous glassy state. It is thought that when the particles have a high $T_g$ material at their surfaces (e.g. a protein typically exhibits $T_{gs}$, above 100° C.), the powder will be able to take up considerable amounts of moisture before lowering the $T_g$ to the point of instability ($T_g$-$T_s$ of less than about 10° C.). Moreover, proteins are desirable for the glassy surface of the particle because strong glasses are more resistant to temperature effects on viscosity. Proteins are considered to be "strong" glasses, as compared to "fragile" glasses, as defined by C. A. Angell in the article mentioned above. See also article by C. A. Angell, *J. Phys. Chem.* 98:13780 (1994).

One aspect of the present invention is a powdered dispersible composition for pulmonary inhalation that exhibits stable dispersibility over time. The composition has a characteristic $T_g$ and $T_s$ wherein the difference between $T_g$ and $T_s$ is at least about 10° C. and preferably is more than about 20° C. The composition comprises a pharmaceutically-acceptable, glassy matrix and at least one pharmacologically active material within the amorphous glassy matrix. Preferably, the composition will comprise a dispersible powder having particles where each dispersed particle exhibits at least an outer region having a glassy phase wherein the mean glass transition temperature is greater than about 35° C. for ambient temperature storage of the powder. By ensuring the composition is substantially in the glassy state the solid state, stability, i.e. dispersibility over time, of the dispersible powder, significantly improves as compared to an amorphous or an amorphous/crystalline composition not in the glassy state.

Having stable dispersibility over time means that the dispersibility of the powdered composition of this invention when packaged as a unit dosage form (e.g. as a "blister pack") does not appreciably change under normal storage condition over the shelf life of the composition. The shelf life of a composition will vary based on a number of factors: the stability of the active material, the interaction of the active with the excipients, the expected storage conditions and the like. The shelf life may vary from a month to 3 years or more, but generally will be about a six months to about 2 years. The measurement of dispersibility is discussed in greater detail hereinafter. The term dispersible is generally viewed as being synonymous with aerosolizable. Generally, the dispersibility is such that the delivered dose obtainable will be at least about 30%, usually at least about 40%, preferably at least about 50% and more preferably at least about 60%. To achieve such delivered dose, the composition of this invention is a powder with the largest particle size less than about 10 microns ($\mu$m) in diameter with a shape that may be spheroidal or "raisin-like" with surface convolutions. The powdered composition of this invention will be composed of particles having a mass median diameter (MMD) of about 1 $\mu$m to about 5 $\mu$m, usually about 1–4 $\mu$m MMD, and preferably 1–3 $\mu$m MMD. The aerosol particle size distribution is about 1–5 $\mu$m mass median aerodynamic diameter (MMAD), usually 1–4 $\mu$m MMAD, and preferably 1–3 $\mu$m MMAD. Preferably the composition exhibits less than about 10% by weight (%w) water, usually below about 5%w and preferably less than about 3%w. Most preferably the composition will contain less than 2%w water. Less water is preferred because the $T_g$ tends to decrease as more water is present. In general, a higher $T_g$ value of the composition is preferred over a lower $T_g$ value. A higher value generally results in greater stability of the dispersibility over time. Preferably the composition exhibits a moisture uptake profile that allows absorption of up to about 5% moisture without a phase change from an amorphous to crystalline form or lowering of $T_g$ to a point which makes the $T_g$–$T_s$ less than about 10° C. Preferably $T_g$–$T_s$ will be more than 20° C. However, it should be understood that the compositions must be protected from significant moisture to be stable. Thus, compositions of this invention should be handled, packaged and stored under conditions that minimize direct contact with water after the compositions have been prepared.

Thus, in handling and packaging the powder, it is important to employ conditions that minimize the presence of water in the environment in which the operations take place. Generally by following the procedures taught in co-pending U.S. applications Ser. No. 08/644,681 filed May 8, 1996 and Ser. No. 08/638,515 filed Apr. 26, 1996, one can minimize problems inherent in the presence of too much moisture. Both of these applications are incorporated herein by reference in their entirety.

Pharmacologically Active Materials

The active drug substances that are preferred are those used for administration via pulmonary inhalation. Such substances include nonmacromolecule pharmaceuticals and macromolecule pharmaceuticals, including small molecules, peptides, glycoproteins, polysaccharides, proteoglycens, proteins, genes and gene vectors. The therapeutically effective amount (i.e. the amount needed to achieve the desired therapeutic effect) of the drug will vary in the composition depending on the biological activity of the drug employed and the amount needed in a unit dosage form. Because the compounds of the present invention are dispensable, it is highly preferred that they be manufactured in a unit dosage form in a manner that allows for ready manipulation by the formulator and by the consumer. Thus, the unit dosage will typically be between about 0.25 mg and 15 mg of total material in the dry powder composition, preferably between about 1 mg and 10 mg. Generally, the amount of active drug in the composition will vary from about 0.05%w to about 99.0%w. Most preferably the composition will be about 0.2% to about 97.0%w active drug.

The pharmacologically active materials useful for preparing the composition of this invention include any active drug administered to achieve the desired physiological effect when administered by inhalation, generally through pulmonary delivery. In the dry state, the phase of the composition containing the active drug may be in crystalline or amorphous form, depending in part on whether the active drug is a macromolecule such as a gene vector, protein, a peptide, or a polypeptide or is a non-macromolecule such as a salt or a small organic molecule. However, in all cases, the outer portion comprising the surface of the dosage form particle is preferably in a glassy form. It may be desirable to prepare the pharmacologically active material in a salt form that forms a glassy matrix itself, e.g. a citrate salt.

Active small molecules for systemic and local lung applications for use with the composition of the present invention are generally drugs of a non-peptide nature and include, but are not limited to, steroids, including, but not limited to, Be estrogen, progesterone, testosterone, dexamethasone, triamcinolone, beclomethasone, beclomethasone dipropionate, fluocinolone, fluocinonide, flunisolide, flunisolide hemihydrate, triamcinolone acetamide, budesonide acetonide, and the like; bronchodilators, including, but not limited to, adrenalin, isoproterenol, metaproterenol, terbutaline and its salts, isoetharine, albuterol and its salts, pirbuterol and its salts, bitolterate, ipratropium bromide, and the like; products and inhibitors of arachidonic acid metabolism such as analgesics, morphine, fentanyl, sumatriptan; mast cell inhibitors, such as cromolyn sodium, and the like; antibiotics, such as, pentamidine isethionate, and the like; alphablockers, retenoids such as retenoic acid; and the like.

Suitable macromolecules, i.e. peptides, polypeptides, proteins (including glycosylated and nonglycosylated proteins and cytokines) and gene vectors include, but are not limited to, calcitonin, erythropoietin (EPO), factor IX, factor VIII, 5-lipoxygenase and cyclooxygenase products and inhibitors, granulocyte colony stimulating factor (G-CSF), granulocyte macrophage colony stimulating factor (GM-CSF), macrophage colony stimulating factor (M-CSF), nerve growth factor (NGF), ciliary neurotrophic factor (CNF), defensins, chemokines, growth hormone releasing factor (GRF), insulin-like growth factor (IGF-1), growth hormone, heparins (regular and low molecular weight), cyclosporin, insulin, leptin and its analogs and inhibitors interferon-α, interferon-β, interferon-γ, interleukins (e.g. interleukin-2 (IL-2), interleukin-3 (IL-3), interleukin-4 (IL-4), interleukin-6 (IL-6), interleukin-11, interleukin-12), interleukin-1 receptor antagonist, interleukin-1 receptor (IL-1R), luteinizing hormone releasing hormone (LHRH) agonists and antagonists, nafarelin, goserelin, leuprolide, somatostatin analog (e.g. octreotide), vasopressin analogs, amylin and analogs, insulinotropin, parathyroid hormone (PTH), peptide Y, gastrins, CCK peptides, thymosin-α-1, IIb/IIIa inhibitors, α-1 antitrypsin, anti-RSV antibody, cystic fibrosis transmembrane regulator (CFTR) gene, integrins, selectins, deoxyribonuclease (DNase), FSH, bactericidal/permeability increasing protein (BPI), and antibodies such as anti-CMV antibody.

Useful active drug substances for use with the composition of the present invention for pulmonary administration also include appropriate gene vectors, such as nucleic acid complexes, i.e., RNA or DNA sequences, that are used for gene therapy. In general, the nucleic acid complex is a DNA associated with an appropriate replication deficient recombinant virus that promotes transfection at the cellular level. Representative DNA plasmids include pCMVβ, pCMV-β-gal (a CMV promoter linked to the *E. coli* Lac-Z gene, which codes for the enzyme β-galactosidase). Representative lipids that promote transfection include dimyristyloxypropyl-3-dimethyl-hydroxyethyl ammonium (DMRIE), dioleoylphosphatidylethanolamine (DOPE), N-[1-(2,3-Dioleyloxy)Propyl[-N,N,N-trimethylammonium chloride (DOTMA), and the like. Such lipids may be used alone or in combination, for example, combinations of DOTMA with DOPE or DMRIE with DOPE. Representative replication deficient transfection viruses include the adenovirus Ad2-CMV-LacZ-2.

Diseases to be Treated by the Compositions of this Invention

Systemic diseases that are suitable targets for treatment with pharmaceutical compounds designed for pulmonary administration, such as the compositions of the present invention, include, but are not limited to, osteoporosis prophylaxis and treatment, Paget's disease, hypercalcemia, anemia, hemophilia B, neutropenia, transplant failure, short stature, renal failure, blood clotting, type I and type II diabetes, hepatitis B and C, multiple sclerosis, chronic granulomatous disease, renal cancer, prostate cancer, endometriosis, pain, ageing, obesity, gastrointestinal cancers, diabetas mellitus, diabetes insipidus, nocturnal enuresis, hypertension, amyotrophic lateral sclerosis (ALS), rheumatoid arthritis, cancer, immunodeficiency disease, acquired immune deficiency syndrome (AIDS), thrombocytopenia, fungal disease, anxiety, hypercholesterolemia, peripheral neuropathies, refractory diarrheas, angina, cystic fibrosis, cytomegalovirus, Kaposi's sarcoma, hairy cell leukemia, migraines, and the like.

Pulmonary diseases that are. suitable targets for treatment with pharmaceutical compounds designed for pulmonary administration, such as the compositions of the present invention, include, but are not limited to, respiratory syncytial virus, CMV, influenza and measles, chronic bronchitis, asthma, adult respiratory distress syndrome (ARDS), fungal disease, tuberculosis, emphysema, pneumocystis carinii, pneumonia, bronchospasm, hay fever, bronchial asthma, pulmonary hypertension, lung cancer treatment and prevention, pulmonary fibrosis, sarcoidosis, chronic obstructive pulmonary disease (COPD) and the like.

In treating these conditions, a therapeutically effective amount of the active agent will be administered, i.e. an amount suffcient to obtain the desired curative, preventative or palliative effect. This amount is easily determined for each active agent by consulting such texts as Goodman and Gilman's "The Pharmacological Basis of Therapeutics," Eighth Edition (1993); The Physician's Desk Reference (1996); and The Merck Manual, Sixteenth Edition (1992).

The Glassy Matrix

The pharmaceutically acceptable matrix used for the composition of this invention may be a single pharmaceutically acceptable excipient or it may be a mixture of such excipients. The matrix will provide the composition with a characteristic $T_g$ that may vary from about 35° C. to about 200° C. Preferably the material will be chosen so that the $T_g$ of the composition is at least about 45° C. and more preferably at least about 55° C. The pharmacologically active material may be in a crystalline or glassy state in the composition as long as the composition's measured $T_g$ is such that the difference between $T_g$ and $T_s$ is at least about 10° C., preferably more than about 20° C. and more preferably more than 30° C. An important aspect of the composition is to include an excipient that is a good "glass former" and is pharmaceutically acceptable. For a glass former, the probability of germinating a crystal rather than forming a glassy solid during the preparation of the glassy matrix is so small that crystals simply tend not to form. While an excipient may be a good glass former, it may also have other characteristics useful for the composition. In addition to the glass former excipient, other additives may be included to aid in stability of the active, adjust the pH (i.e. a buffering agent), improve dispersibility, aid in providing uniformity of delivery, and other purposes.

The combination of materials used in the composition of this invention will assist in providing stability of the drug dispersibility of the composition, consistency of the composition and uniform pulmonary delivery of the composition. The total amount of glass formers and additives needed will vary depending on the nature of the drug, i.e its structure, potency, activity, and the like. These excipients are generally chosen to be relatively free-flowing particulate solids, that do not thicken or polymerize upon contact with water, are toxicologically innocuous when inhaled as a dispersed powder and do not significantly interact with the active agent in a manner that adversely affects the desired physiological action of the drug. The amount of non-drug materials useful for preparing the composition of the present invention will serve to uniformly distribute the drug throughout the composition so that it can be uniformly dispersed when it is to be delivered into the lung. It will preferably also serve to dilute the active agent to a concentration at which the active agent can provide the desired beneficial palliative or curative results while at the same time minimizing any adverse side effects that might occur from too high a concentration. Thus, for an active drug that has a high physiological activity, more of the excipients will be employed. For an active agent that exhibits a lower physiological activity a lesser quantity of the excipients will be employed. The glass former may be used alone or in combination with the additives, which may be crystalline or amorphous.

While a number of pharmaceutically acceptable additives are acceptable for use with the composition of the present invention, the composition will generally be substantially free of any "penetration enhancers" which are undesirable for dosage forms intended for pulmonary absorption. Penetration enhancers are surface active compounds which promote penetration of a drug through a mucosal membrane or lining and are proposed for use in intranasal, intrarectal, and intravaginal drug formulations. Types of penetration enhancers include, but are not limited to, bile salts, e.g., taurocholate, glycocholate, and deoxycholate; fusidates, e.g., taurodehydrofusidate; and biocompatible detergents, e.g., tweens, Laureth-9, and the like. The use of penetration enhancers in formulations for the lungs is generally undesirable because the epithelial blood barrier in the lung can be adversely affected by such surface active compounds. The powder compositions of the present invention are readily absorbed in the lungs without the need to employ penetration enhancers.

Some additives that are useful as stabilizers for protein drugs such as the interferons include polypeptides of molecular weight of about 1,000 to about 100,000. Particularly valuable is human serum albumin (HSA), which not only stabilizes active protein drugs but also increases the dispersibility of a composition. See U.S. patent application Ser. No. 08/423,568, filed Apr. 14, 1995, which is incorporated herein by reference. Other stabilizers include certain carbohydrates such as mono-saccharides, disaccharides and polysaccharides. These are believed to help protect the structure of the protein. Some of these materials may also act as bulking agents and glass formers, as discussed hereinafter.

Suitable additives for use with the composition of the present invention include, but are not limited to, compatible carbohydrates, natural and synthetic polypeptides, amino acids, polymers, or combinations thereof. Suitable carbohydrates include monosaccharides, such as galactose, D-mannose, sorbose, dextrose, and the like. Monosaccharides will be present in small amounts to minimize the depression of the $T_g$. Disaccharides, such as lactose, trehalose, maltose, sucrose, and the like are also useful and are also useful glass formers. Others include cyclodextrins, such as 2-hydroxpropyl-β-cyclodextrin; polysaccharides, such as raffinose, maltodextrins, dextrans, and the like; and alditols, such as mannitol, xylitol, sorbitol, and the like. A preferred group of carbohydrates includes lactose, trehalose, raffinose, maltodextrins, and mannitol. Suitable polypeptides include aspartame. Suitable amino acids include any of the naturally occurring amino acids that form a powder under standard pharmaceutical processing techniques and include the non-polar (hydrophobic) amino acids and the polar (uncharged, positively charged and negatively charged) amino acids. Such amino acids are of pharmaceutical grade and are generally regarded as safe (GRAS) by the FDA. Representative examples of non-polar amino acids include alanine, isoleucine, leucine, methionine, phenylalanine, proline, tryptophan, and valine. Representative examples of polar, uncharged amino acids include cysteine, glutamine, serine, threonine, and tyrosine. Representative examples of polar, positively charged amino acids include arginine, histidine, and lysine. Representative examples of negatively charged amino acids include aspartic acid and glutamic acid. Of these, glycine, aspartic acid and glutamic acid are preferred. Suitable synthetic organic polymers include poly[1-(2-oxo-1-pyrrolidinyl)ethylene, i.e. povidone or PVP.

Suitable pH adjusters or buffers include inorganic and organic acids, salts and bases. Organic acids and organic salts, prepared from organic acids and bases, include e.g. citric acid, sodium citrate, sodium gluconate, sodium ascorbate, and the like. Organic buffers are preferred over inorganic buffers. Sodium citrate is preferred for pH 2–7 and sodium citrate/glycine for pH about 7–9.

Glass formers suitable for use with the compositions of the present invention will generally be substances that have a relatively high glass transition temperature ($T_g$), such that the $T_g$ of the entire dosage form, i.e. the mean glass transition temperature, will be sufficiently high to remain above the temperatures to which the composition will be subjected during storage. The choice of a suitable glass former will greatly depend on the nature of the active drug. Preferable glass formers will have glass transition temperatures that will yield compositions with mean glass transition temperatures above about 35° C. and preferably above about 45° C. Thus, in the majority of cases, ratios of excipients required to accompany the active drug for any of the purposes previously mentioned will be identified first. Consequently, a suitable glass former will be chosen as well as the appropriate percentage of the composition it should comprise to obtain an acceptable glass transition temperature. In many cases the glass transition temperature of each of the excipients, active drug, and glass former will be known and a ratio of glass former to excipients can be relatively easily estimated and subsequently tested. The key is to produce a composition that will 1) be in a glassy state in at least the outer surface of a given particle of the aerosol powder and 2) have a $T_g$ sufficiently above the $T_s$ such that the composition will not likely be physically degraded and will instead retain a relatively stable morphological structure to ensure consistent dispersibility over time.

Glass formers suitable for use with the compositions of the present invention include certain materials that also are bulking agents. These are materials that are pharmaceutical grade and generally regarded as safe (GRAS) by the FDA. These include but are not limited to, carbohydrates, carbohydrate derivatives, carbohydrate polymers, synthetic organic polymers, organic carboxylic salts, proteins, polypeptides, peptides, and high molecular weight polysaccharides. While carbohydrates such as monosaccharides (e.g. galactose, D-mannose, sorbose, dextrose and the like) are useful in small amounts as additives and may act to stabilize the conformation of large proteins, they are generally not good glass formers. Their $T_g$ values are too low, often less than about 25° C. In general, $T_g$ is a function of molecular weight, with higher molecular weight materials having a higher $T_g$. However, once the molecular weight of a glass former goes above about 3000, the $T_g$ does not appear to increase at the same rate, if at all. Some excipients may not be good glass formers alone, but may be useful when combined with other excipients that tend to keep the combination in the glass state. For example, mannitol alone is not a good glass former, but when combined with glycine (e.g. about a 1:1 w/w ratio) the combination may be useful as a glass former. Suitable carbohydrates, carbohydrate polymers and carbohydrate derivatives include, but are not limited to, compounds that generally have at least 11 carbons or more with a molecular weight of up to about 100,000 or more. Examples include disaccharides, such as lactose, trehalose, maltose, sucrose, and the like; cyclodextrins, such as 2-hydroxypropyl-β-cyclodextrin; polysaccharides, such as raffinose, maltotriose, stachyose, maltodextrins, dextrans, and the like; glucopyranosyl-alditols, such as glucopyranosyl-mannitol, glucopyranosyl-sorbital and the like. Very high molecular weight polysaccharides having a modified structure are also useful. These excipients include heparin (a sulfated polysaccharide) and hyaluronic acid (a muco-polysaccharide). A preferred group of carbohydrates includes lactose, raffinose, trehalose, maltodextrin, sucrose, maltose, stachyose, polydextrose, cyclodextrin, glucopyranosyl-mannitol, hydroxyethyl starch and glucopyranosyl-sorbitol. Particularly useful glass formers include the salts of organic acids such as lactic acid, ascorbic acid, maleic acid, oxalic acid, malonic acid, malic acid, succinic acid, citric acid, gluconic acid, glutamic acid, and the like. Salts may include cations such as sodium, potassium, calcium, magnesium, and the like. Generally anions with high basicity are preferred. Sodium salts are preferred over potassium salts. Divalent cations form glasses more readily. Examples of representative acid salts include sodium citrate, sodium lactate, sodium maleate, magnesium gluconate, sodium ascorbate, and the like. The preferred salt will have a high stability constant and sufficient solubility to inhibit crystallization and thereby form the glassy matrix. In some cases mixtures of cations may be useful (e.g. calcium and sodium salts).

Other useful glass formers include proteins and polypeptides. These include HSA, polyamino acids (e.g. polyalanine, polyarginine, polyglycine, polyglutamic acid and the like), casein, collagen, gelatin, purified gelatin proteins (e.g. BYCOS®), and some pharmacologically active compounds (e.g. insulin). In some cases (e.g. insulin) the active itself is a glass former and assists in forming the glassy matrix. Other suitable glass forming excipients include hydroxypropyl-($\beta$-cyclodextrin (HP-$\beta$-CD), albumin, povidone, pectin, polyethyleneglycol (PEG), Ficol® polymer (see U.S. Pat. No. 3,300,474 which is incorporated herein by reference), and the like. The most preferable glass formers are sodium citrate, trehalose, povidone, sucrose, lactose, maltodextrin, and raffinose. Ideally, compounds that are GRAS compounds are preferred over those that are not GRAS. However, particularly suitable non-GRAS compounds should not be eliminated if they can become GRAS compounds in the future.

It should be noted that although a preferred glass former may already be part of the formulation for other purposes, it may not be of the proper percentage to provide the desired characteristics of the present invention to stabilize the solid state dispersibility over time of the composition. The determination of the proper amount of glass former should be made after the initial formulation is chosen. For example, raffinose can be used to stabilize a labile protein, such as I-1-1 Receptor, in a formulation. Raffinose may also be preferred to comprise the glass former to obtain the added benefit of stabilizing dispersibility over time. However, the amount required for this purpose may differ significantly from the amount required to stabilize the protein active drug. Alternatively, it can be the case that a combination of raffinose with another glass former, such as sodium citrate, is more preferred to comprise the composition, wherein only raffinose is needed to stabilize the protein active drug. Additionally, it may be advisable to change the stabilizer previously used for a given formulation where the added benefit of stabilizing the stability of dispersibility over time is desired. If the preferred glass former can also suitably stabilize a labile protein active drug, it could simplify and minimize the expense of formulation to use the same carbohydrate, for instance, to both chemically stabilize the labile protein and provide dispersibility stabilization, wherein the concentration of carbohydrate chosen is suitable for both functions. Of course, for small molecules, no stabilizer for the drug active is typically required, thus the choice of a glass former is more straight forward.

In one preferred embodiment of the present invention, a protein active drug, such as insulin, is combined and spray dried with a suitable additive, such as mannitol; a suitable protein stabilizer, such as sodium citrate; and a suitable buffer, such as glycine. As previously discussed, the choice of components of an aerosol powder formulation depends on the nature of the active drug. In the case of a protein, its chemical and physical stability is critical as well as its dispersibility within the dosage form. In the case of a preferred embodiment of the present invention the protein will be spray dried rather than lyophilized. Thus, the stability of the protein during the spray drying process is not as tenuous as during a lyophilization process. Once in the dosage form, the chemical and physical stability of the protein can be maintained by using methods and excipients well known in the art and previously mentioned.

Dispersibility itself can be enhanced by a number of methods, including the use of bulking agents. Human serum albumin for instance has been found to be an excellent dispersibility enhancer.

Selection of the glass former to maintain a stable dispersibility over time will depend on the nature of the composition described above. A glass former will be chosen that will yield a mean glass transition temperature of the entire composition sufficiently high to ensure that the highest temperature for the labeled storage conditions for the composition is essentially below the glass transition temperature, i.e. about 10° C. less. The lower a composition is below its glass transition temperature, the more stable it is. The glass transition temperature of a composition will depend on the nature of the glass former, other excipients, and the active drug and on the amount of moisture in the composition. Generally, the presence of moisture within the composition will decrease its glass transition temperature. Additionally, a composition will typically absorb some moisture over time. Thus, glass formers indicated above as preferred have glass transition temperatures that are sufficiently high for most formulations.

Another aspect of this invention is the combination of the powdered composition of this invention with a pharmaceutically-acceptable carrier having a particle size that is not respirable, i.e. is of such a size that it will not be taken into the lungs in any significant amount. This can be viewed as a uniform blend of smaller particles of the glassy matrix (e.g., less than 10 $\mu$m, preferably between 1–5 $\mu$m MMD and MMAD) with larger particles of the carrier (e.g., about 15–100 $\mu$m, preferably about 25–27 $\mu$m). Such a blend improves the flow characteristics of the blend in filling the blister packs of a unit dosage form. Upon dispersion, the smaller particles are then respired into the lungs while the larger particles are generally retained in the mouth. Carriers suitable for blending include crystalline or amorphous excipients that have an acceptable taste and are toxicologically innocuous, whether inhaled or taken orally. Crystalline carriers are preferred and include, e.g., the saccharides, disaccharides, and polysaccharides. Representative examples include lactose, mannitol, xylitol and the like.

Table I lists glass transition temperatures for suitable glass formers and preferred glass formers.

| Glass Former | Glass Transition Temperature° C. |
| --- | --- |
| Sucrose | 56 |
| Polydextrose | 56 |
| Glucopyranosyl-mannitol | 57 |
| Glucopyranosyl-sorbitol | 60 |
| Maltotriose | 76 |
| Cellobiose | 77 |
| Trehalose | 77 |
| Dextran | 83 |
| Raffinose | 90 |
| Sodium Citrate | 106 |

In preparing the compositions of this invention, the pharmacologically active material will be present in an amount that will range between about 0.05%w for a drug that is not very active material to about 99%w for a drug that is not very active and is a glass former itself. Generally, the range will be from about 0.2%w to about 97.0%w, preferably about 0.5%w to about 90%w. The remainder of the material will be the glassy former, thus forming the glassy matrix, within which the drug is found. The matrix will provide the composition with its characteristic $T_g$. The material comprising the glassy matrix will be up to 100%w glass former with additives included as needed. For most compositions additives will be present in the matrix at a level of less than about 20%w.

Determining $T_g$

In general $T_g$ for a composition is determined using differential scanning calorimetry (DSC). As discuss hereinbefore, in using DSC techniques the onset, midpoint or endpoint of the change in Cp in the transition can be used, as long as the technique uses the point consistently. In the DSC measurements in this application, the onset of the change in specific heat, Cp, is the reported glass transition temperature. In the DER measurements, the midpoint is used such as DSC techniques useful for measuring $T_g$ are known in the art and can be found in the book entitled "Thermal Analysis" by Bernard Wienderlich, Academic Press, 1990, which is incorporated herein by reference. Adjustments may be made to reflect the conditions and equipment of a particular facility.

Another technique for determining $T_g$ is thermal mechanical analysis (TMA), which measures expansion or contraction of a solid on warming or cooling. This is a less expensive technique but less valuable for powder compositions due to compaction problems with powders. It is difficult to observe the volume expansion at the $T_g$ when a powder is warmed through its glass transition temperature. Only the softening or collapse of the powder is observed at temperatures several degrees higher than the $T_g$.

A third technique for determining $T_g$ is dielectric relaxation (DER) analysis, which is sometimes abbreviated with the initials DEA. Generally, this technique is particularly useful for protein-based glassy matrixes. DER analysis is described in the book entitled "Dielectric Analysis of Pharmaceutical Systems," by Duncan Q. M. Craig, Taylor and Francis, 1995, which is incorporated herein by reference.

Composition in Combination with Labeling Instructions

Another aspect of this invention is a unit dosage form powdered aerosol composition having stable dispersibility over time in combination with labelling instructions for treating pulmonary or systemic disease in a mammalian subject. The composition exhibits a characteristic $T_g$ and a storage temperature ($T_s$) that is recommended in its approved labelling, with the difference between $T_g$ and $T_s$ being at least 10° C. As discussed herein, the composition is a pharmacologically active material within a glassy matrix. As previously mentioned, the FDA requires that a drug product be delivered to a site of action at an amount within a suitable range of its indicated delivered dose. This suitable range is characterized by a delivered dose of 85%–115% of the labeled dose. Dosage forms prepared with the compositions of the present invention will usually provide a formulation that complies with these FDA requirements. More importantly the compositions of the present invention will provide for a dosage form that maintains dispersibility longer and thus has a longer shelf life. This is a key aspect of the invention in that before a compound can be approved for any particular use, it must be approved for marketing by the FDA. Part of that process includes providing a label, as defined in 21 Code of Federal Regulations (CFR) §201, that will accompany the pharmaceutical composition which is ultimately sold. While the label will include a definition of the composition and such other items, such as the clinical pharmacology, mechanism of action, drug resistance, pharmacokinetics, absorption, bioavailability, contraindications, and the like, it will also generally provide the necessary dosage, administration, usage and storage temperature. For example, 21 CFR §341.76(c)(2) provides that labeling of bronchodilator drug products for pulmonary inhalation via a pressurized metered-dose aerosol container be labeled to indicate that each inhalation (dose) contain the equivalent of 0.16 to 0.25 mg of epinephrine. In order for this requirement to be met, the drug must be sufficiently dispersed in the formulation and the stability of the dispersion over time must be maintained so as to consistently deliver a dose within the range specified above. Thus, the combination of the drug with appropriate labelling instructions is important for proper usage of the drug once it gets to the market.

Process for Preparing Compositions of the Invention

Another aspect of this invention is a process for producing a powdered dispersible composition having stable dispersibility over time by removing the solvent from a solution of the composition under conditions sufficient to maintain the composition in an amorphous form until sufficient moisture is removed to form a glassy state.

In preparing the composition of this invention conditions and materials are used that provide a composition that exhibits a $T_g$ that is at least about 10° C. greater than the recommended storage temperatures ($T_s$). Usually this storage temperature is at ambient temperature of about 25° C. To have a difference between $T_g$ and $T_s$ of 10° C., the $T_g$ is about 35° C. For a difference of about 20° C. greater than ambient, $T_g$ is about 45° C. and for a difference of at least about 30° C., the $T_g$ is about 55° C. The compositions preferably have higher $T_g$ values to better maintain dispersibility over time under adverse conditions such as higher temperatures and greater relative humidity (RH). Preferably, processing techniques that provide a powder composition having particles with a material (e.g., a protein) on the surface showing a particularly high $T_g$. Having particles with the majority of glassy state material on surface is important for at least two reasons: (1) this provides a composition with a higher $T_g$ that allows for a larger amount of water to be added without reducing the $T_g$ below the desired level and (2) this provides greater resistance to viscosity changes with increased temperature. This results in a composition that maintains its dispersibility over time in spite of high RH or temperature swings.

In general, the solvent removal process techniques that are useful include spray drying; lyophilization followed by milling to micronize the powder; atomization onto a cold surface, followed by sublimation and collection of the micronized powder; evaporative drying of a non-frozen solution in a vacuum oven or centrifugal evaporator maintained at temperatures where the solution does not freeze (5 to 50° C.), followed by milling; atomization of a chilled or non-chilled aqueous drug solution into an organic suspending medium containing a solubilized protein, whereafter the organic medium is evaporated and the powder milled to respirable particle size. The resultant powder particles are glassy or crystalline internally with a majority of the glassy matrix glass coating on the surface. Similarly, cosolvent precipitation techniques and evaporation/milling may be used to produce similar particles.

The preferred method for preparing a dispersible powdered composition of this invention comprises spray drying a homogenous aqueous mixture comprising water (with or without an organic solvent), a glass forming excipient, and an active agent suitable for treating a disease state by inhalation under conditions sufficient to provide a dispersible powered pharmaceutical composition having a particle size less than about ten microns with the MMD and MMAD range discussed herein.

The spray drying method generally consists of bringing together a highly dispersed liquid, which is the aqueous composition defined above, and a sufficient volume of hot air to produce evaporation and drying of the liquid droplets. The feed liquid may be a solution, colloidal suspension or emulsion provided the feed is capable of being atomized. Preferably a solution is employed. In general the feed is sprayed into a current of warm filtered air that evaporates the water and conveys the dried product to a collector. The spent air is then exhausted with the moisture. While, in general, the resulting spray-dried powdered particles are homogenous, approximately spheroidal in shape and nearly uniform in size, the improvement of this invention result in particles that are comprised of a glassy matrix and are irregular in shape. A further discussion of spray drying can be found in Chapter 89 of *Remington's* at pages 1646–47. It is found that the process of this invention works particularly well using a Buchi Model 190 or Niro Mobile Minor spray dryer, modified to operate at high air flow rates. Generally, the inlet temperature and the outlet temperature are not critical but will be of such a level to result in a composition having the desired $T_g$. The inlet temperature, solution composition of the formulation, and feed rate are parameters which are adjusted to achieve a given outlet temperature (which results in a powder with the desired moisture content). Atomization air flow, solution composition of the formulation, and feed rate are adjusted to achieve the desired particle size. The spray dryer inlet temperatures thus may be between temperatures of about 80° C. to about 200° C., with the outlet temperature being at temperatures of about 50° C. to 100° C. Preferably, these temperatures will be from 90° C. to 180° C. for inlet and rom 50° C. to 90° C. for outlet. The powder processing conditions are adjusted as described above for both scales of production (e.g. the feed flow rate for the Buchi was 3 to 6 mL/minute and about 10-fold that flow rate for the Niro batch scale and atomizer air flow rate was 700–800 LPH (liters per hour) for the Buchi and 12 scfm at 43–47 psig for the Niro). Secondary drying or vacuum drying may be employed, but is not needed.

By following the general process teachings above one obtains a composition having the desired particle size $T_g$, and dispersibility characteristics to be respirable and suitable for pulmonary delivery to a subject in need thereof.

Dispersibility Determination

To determine the dispersibility of a composition of this invention as compared to other compositions, one can use a standard test for quantifying the deliverable dose of a unit dosage form by aerosolizing a powder composition, collecting the aerosolized composition and measuring the delivered material using the equipment and procedure as described hereinafter.

A high level of dispersibility leads to a high percentage of delivered dose of a composition of this invention. Delivered dose is a key parameter in the success of a powdered composition. It is a measure of the efficiency by which a composition is delivered by a dry powder pulmonary inhaler device to (1) extract the test powder from a dosage receptacle such as a blister package, (2) aerosolize that powder into a "standing cloud" of fine particles in an aerosol chamber, (3) deliver those fine particles through the mouthpiece of the device during a test inhalation. The dose delivered with each formation tested is generally determined as follows using a device wherein a single blister pack, filled with approximately 5 mg of powder, is loaded into the device, The device is actuated, suspending the powder into the device's aerosol chamber. The "standing cloud" of fine particles is then drawn form the chamber at an airflow rate of 30 L/min for 2.5 seconds (1.25 L inspired volume) and the sample collected on a suitable filter, a polyvinylidene fluoride membrane filter with a 0.65 µm pore size is particularly useful. The sampling airflow pattern is controlled by an automatic timer and operated to simulate a patient's slow deep inspiration. The overall efficiency (delivered dose) and percent of the powder left in the blister pack after actuation is determined gravimetrically by weighing the powder on the filter and the amount of powder left in the blister pack. This process may be visualized as follows:

5 mg. powder in blister pkg. → suspended by device into chamber → "inhaled" onto filter → filter weighed __% left in blister   __% left in device   __% collected on filter The calculation of dispersibility is as follows:
1. Total mass of powdered composition in a unit dosage (e.g., a 5 mg blister pack).
2. Total mass of powdered composition aerosolized in a unit dosage and collected on the filter (e.g., 2.5 mg)
3. Dispersibility is defined as the mass of powder collected on the filter divided by the mass of powder in the blister expressed as a percent. (e.g., 2.5÷5=50%).

Equipment that is suitable (with minor modifications) for use in determining dispersibility is described in PCT application published as International Patent Number WO 93/00951, published Jan. 21, 1993 entitled Method and Device For Aerosolized Medicaments by John S. Patton. That application in its entirety is incorporated herein by reference.

Particle Size Determination

Particle size can be measured by any one of various methods known to those of ordinary skill in the art. For example, particle size distribution of the bulk power is measured by liquid centrifugal sedimentation in a particle size analyzer. Particle size can also be characterized using a scanning electron microscope (SEM). By using SEM, the surface morphology can also be examined. However, only a few particles can be examined by SEM requiring other methods to be used to quantitatively determine particle size distribution.

The aerosol particle size determination is done using a cascade impactor, e.g. a model made by California Measurements or Graseby Anderson.

EXAMPLES

Example 1

This example describes a 20% insulin formulation for which the difference between $T_g$ and $T_s$ is less than 10° C. This resulted in a formulation that, although chemically stable, did not have stable dispersibility over the desired shelf life of the product at standard recommended storage temperature ($T_s$) testing conditions.

A 20% insulin aerosol formulation was obtained by preparing a solution of human zinc insulin, mannitol, sodium citrate dihydrate, and citric acid monohydrate. Bulk crystalline human zinc insulin, obtained from Eli Lilly and Company, Indianapolis, Ind., and U.S.P. grade excipients were used. The solution contained 1.5 mg insulin, 4.96 mg mannitol, 1.04 mg citrate buffer (sodium citrate and citric acid) per milliliter of deionized water for a total solids concentration of 7.5 mg/mL at pH 6.7. A dry powder was prepared by spray-drying the aqueous solution using a Buchi Laboratory Spray Dryer—Model 190 under the following conditions:

| | |
|---|---|
| Temperature of aqueous solution | 2–8° C. |
| Inlet temperature | 123° C. |
| Outlet temperature | 81° C. |
| Feed rate | 5.3 mL/min |
| Jacketed cyclone temperature | 30° C. |

After all the aqueous solution was pumped into the spray dryer, the outlet temperature was maintained at 85° C. for 10 minutes by slowly decreasing the inlet temperature to provide a secondary drying.

The resultant dry powder aerosol formulation contained the following solids content:

20.0% insulin, 66.2% mannitol, 13.1% sodium citrate, 0.7% citric acid

Characterization and Stability

Insulin powders were packaged in foil pouch barrier packaging with desiccant. The pouches were stored at 30° C., 40° C., and at temperature cycling conditions of 2 to 37° C. every 24 hours. Stability samples were evaluated for insulin content and purity using reversed phase HPLC, moisture content, aerosol performance based on delivered dose of insulin, and glass transition temperature using differential scanning calorimetry.

Reversed phase HPLC analysis using a stability-indicating method for insulin showed no changes in the insulin content or purity at any of the storage conditions tested. After storage, the insulin content accounted for 99% of the expected insulin. For one batch of the citrate/mannitol powder stored for 22 months at ambient room temperature, the insulin purity was 99% initial with trace amounts of degradation products appearing in the chromatogram.

Moisture content was measured by a coulometric Karl Fisher method using a Mitsubishi CA-06 Moisture Meter. Dry powder aerosols prepared using these process conditions resulted in compositions containing 0.5% to 1.5% moisture.

Figure 1B:
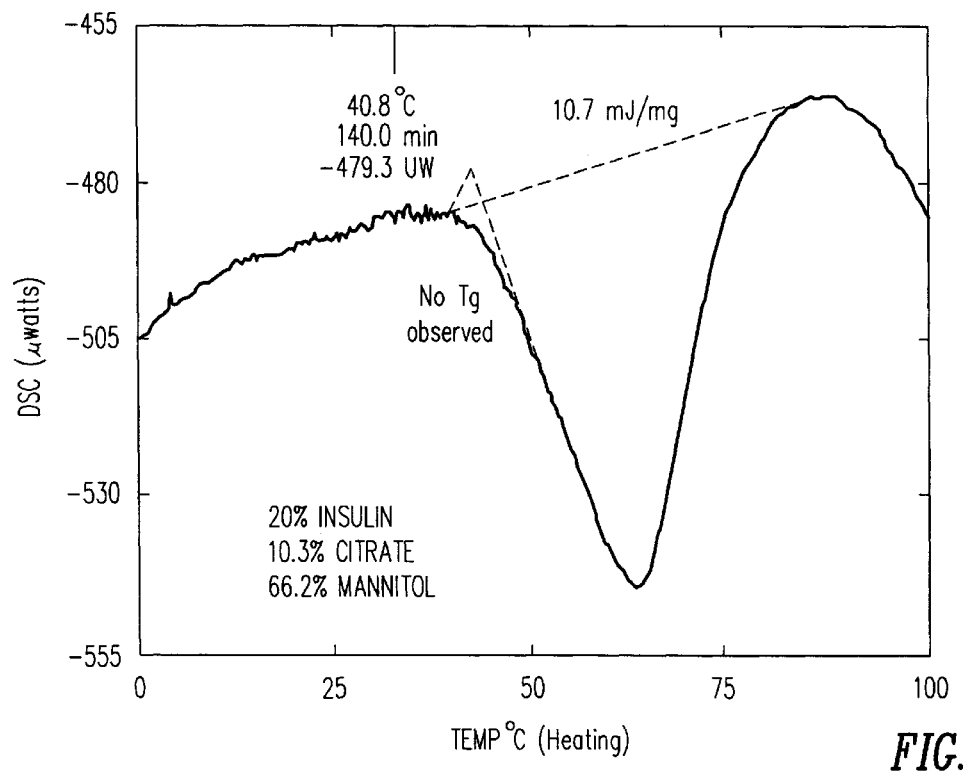
FIG. 1B is a DSC thermogram of the same formulation shown in FIG. 1 aged for two weeks under temperature cycling from 2–37° C.

Thermal analysis using differential scanning calorimetry (DSC) was carried out using a Seiko calorimeter calibrated using nitrogen purge gas and indium as a standard reference. Powder samples (10–20 mg) were hermetically sealed in aluminum pans, cooled to <−50° C. and then heated at 1° C. per minute. Thermograms were generated as the samples were heated. The glass transition temperatures of freshly prepared powders formulations were in the range of 28 to 34° C. (at 0.4 to 1.4% moisture). X-Ray diffraction and microscopic analysis showed that the powders were partially crystalline and a melting endotherm for mannitol was observed at about 150° C. by DSC. More importantly, DSC analysis showed a loss of the glassy state for these powders after storage for a few weeks at 30° C., 40° C., or with temperature cycling from 2 to 37° C. Thermograms of the initial and aged formulation are shown in FIGS. 1A and 1B. In the thermogram of the initial sample (FIG. 1A), a glass transition temperature with onset of about 32° C. is observed, followed by an enthalpic relaxation of the glass at 33° C. In contrast (FIG. 1B), the powder aged for 2 weeks under temperature cycling from 2–37° C. showed a broad endotherm at 41 ° C., i.e. the loss of glass transition. Similar results were obtained at all storage conditions.

The delivered dose of the insulin powder compositions was measured by collecting the aerosol powder produced by a dry powder dispersion device on a filter placed over the device mouth piece. This measurement is similar to devices described in U.S. application Ser. Nos. 07/910,048; 08/313,707; 08/309,691 and PCT/US92/05621, the disclosures of which are incorporated herein by reference. The delivered dose of the insulin powder composition was determined as the mass percentage of the total powder (5.0 mg) loaded into the device. Aerosol and DSC data are presented below. Aerosol delivered dose for these powder compositions decreased significantly upon storage. Concurrent DSC analysis showed that the initial glassy powders quickly (<1 month) converted to the rubber state.

| Composition Code | Insulin Content | Storage Condition | Delivered Dose (%) | Moisture Content (%) | $T_g$ by DSC |
|---|---|---|---|---|---|
| I-001 (lot # R156-15A) | 20.0 | initial | 70.6 ± 4.0 | 1.0 | 28 |
| | | 2 week; cycling 2–37° C. | 56.7 ± 2.9 | 0.7 | |
| | | 4 week; 30° C. | 51.2 ± 12.5 | 0.5 | none |
| | | 4 week; 40° C. | 35.9 ± 9.1 | 1.4 | none |
| | | 12 week; 30° C. | 45.1 ± 5.4 | 0.5 | |
| I-001 (lot # R95008) | 20.0 | initial | 72.4 ± 1.5 | 0.4 | 32 |
| | | 2 week; cycling 2–37° C. | 62.9 ± 2.6 | 0.5 | 32 |
| | | 4 week; 30° C. | 69.3 ± 1.8 | 0.7 | not done |
| | | 8 week; 30° C. | 68.7 ± 3.0 | 0.7 | 32 |
| | | 4 week; 40° C. | 49.7 ± 3.0 | not done | none |

Example 2

This example sets forth a 20% insulin composition of this invention that maintained protein integrity and aerosol stability after storage at 30° C., 40° C., 50° C., and temperature cycling at 2 to 37° C. ($T_g-T_s$>>30° C.).

A 20% insulin aerosol formulation was obtained by preparing a solution of human zinc insulin, mannitol, sodium citrate dihydrate, and citric acid monohydrate. Bulk crystalline human zinc insulin, obtained from Eli Lilly and Company, Indianapolis, Ind., and U.S.P. grade excipients were used. The solution contained 2.0 mg insulin, 1.82 mg mannitol, 5.91 mg sodium citrate, 0.006 mg citric acid, and 0.26 mg glycine per milliliter of deionized water for a total solids concentration of 10.0 mg/mL at pH 7.3. Dry powders were prepared by spray-drying the aqueous solution using a Buchi Laboratory Spray Dryer under the following conditions:

| | |
|---|---|
| Temperature of aqueous solution | 2–8° C. |
| Inlet temperature | 128–130° C. |
| Outlet temperature | 85–88° C. |
| Flow feed rate | 5.0 mL/min |
| Jacketed cyclone temperature | 30–31° C. |

After all the aqueous solution was pumped into the spray dryer, the outlet temperature was maintained at 85° C. for 5 minutes by slowly decreasing the inlet temperature to provide a secondary drying.

Larger batches of powder were prepared by spray-drying a solution containing 2.5 mg insulin, 2.28 mg mannitol, 7.39 mg sodium citrate, 0.007 mg citric acid, and 0.32 mg glycine per milliliter of deionized water for a total solids concentration of 15.0 mg/mL at pH 7.3. A Niro Spray Dryer was used to prepare the dry powder using the following conditions:

| | |
|---|---|
| Temperature of aqueous solution | 2–8° C. |
| Atomizer chilling water return | 2–6° C. |
| Inlet temperature | 143–147° C. |
| Outlet temperature | 79–81° C. |
| Atomizer air flow | 12 scfm at 41–47 psig |
| Flow rate | 50 mL/min |

Both the Buchi and Niro dry powders (I-004) contained the following solids content:
20.0% insulin, 2.6% glycine, 59.1% sodium citrate, 18.2% mannitol, 0.1% citric acid Characterization and Stability Insulin powders were stored desiccated at <10% relative humidity (unless noted) at 30° C., 40° C., 50° C. and at temperature cycling conditions of 2 to 37° C. every 24 hours. Stability samples were evaluated for moisture content, aerosol performance based on delivered dose of insulin, and glass transition temperature using differential scanning calorimetry.

Thermal analysis using differential scanning calorimetry (DSC) and aerosol delivered dose testing were carried out as described previously. The aerosol particle size distribution was measured using a cascade impactor (California Measurements IMPAQ-6) connected to the device described for delivered dose testing.

Figure 2:
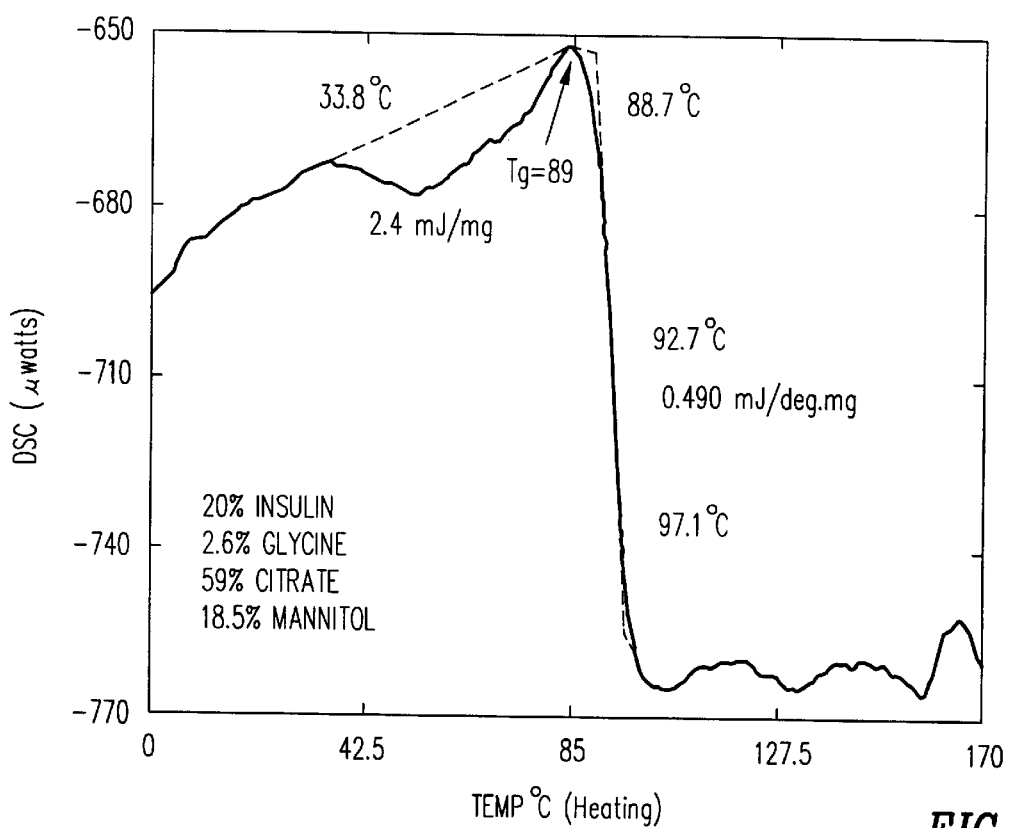
FIG. 2 shows a DSC thermogram of an insulin composition of this invention.
Figure 3:
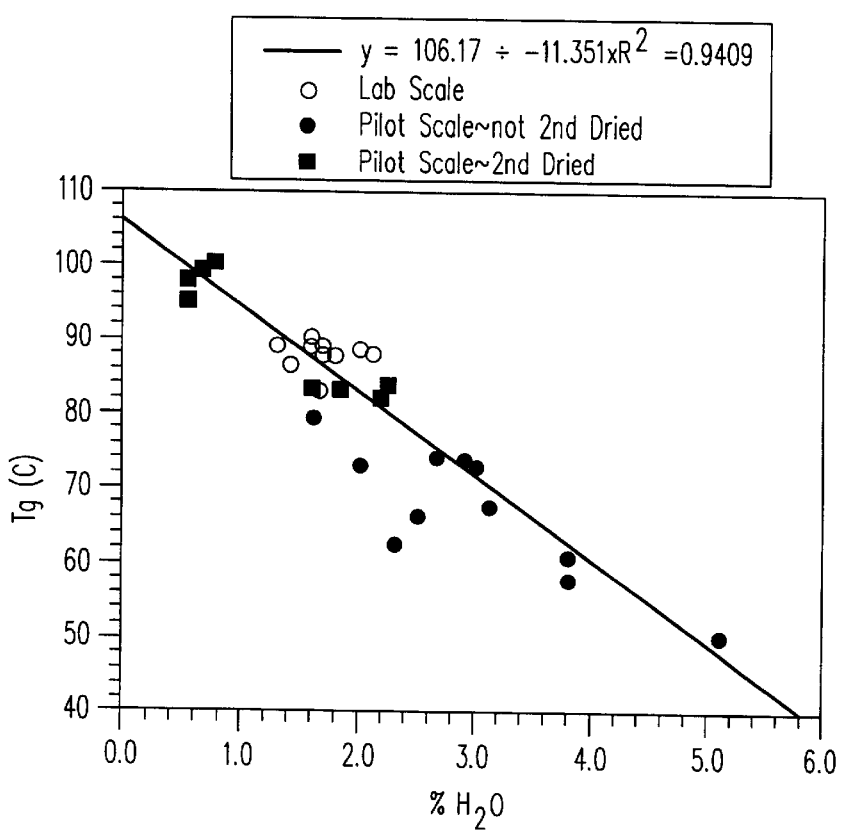
FIG. 3 shows a $T_g$ moisture profile of a composition of this invention described in Example 2.

Stability data are summarized below for several powders of this composition prepared on both the Buchi and Niro spray dryers. Within the error of the measurements, the aerosol performance remained unchanged upon storage. FIG. 2 shows a DSC thermogram of this insulin formulation stored at 40° C. at the 3–4 week timepoint and indicating a $T_g$ of 89° C. The small endotherm preceding the glass transition appeared in all thermograms. It may be due to desorption of water or a denaturing of a small amount of insulin not in the glass phase. A plot of moisture content as a function of glass transition temperature is shown in FIG. 3. This formulation was remarkable in the fact that the powder could take up >5% moisture without loss of aerosol performance (delivered dose 72%; MMAD 2.4 μm with 79% less than 5 μm).

Figure 4:
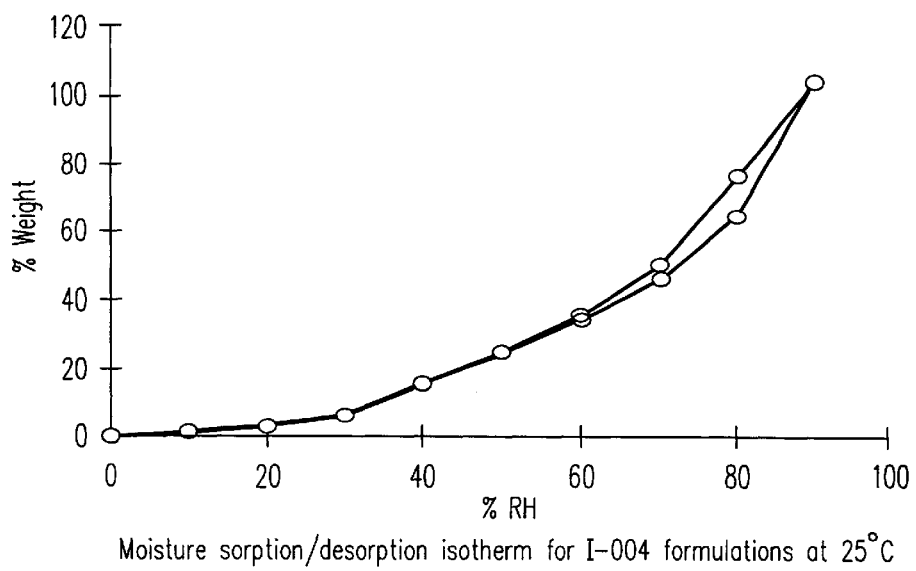
FIG. 4 shows a graph of the moisture absorption/desorption isotherm for a formulation of this invention described in Example 2.

The effect of moisture on $T_g$ is material specific and must be known in order to achieve a good aerosol product. Even for a glassy material with a high $T_g$, the potential for crystallization and glass relaxation to the rubbery phase increases with increasing moisture content. The compositional phase diagram for this formulation was characterized by analyzing powders prepared by two methods: 1) exposure of powder to humid storage conditions and 2) preparation of powders at different moisture contents by altering secondary drying conditions. The results of DSC and moisture analysis are shown in the $T_g$-moisture profile of FIG. 3, showing that the $T_g$ should be above 40° C. at moisture contents up to about 4.5 to 5%. The effect of moisture on the powder was further tested by moisture sorption analysis over a range of 10 to 90% at 25° C. (FIG. 4). All the water that is adsorbed can also be desorbed indicating that the powder does not undergo amorphous to crystalline phase changes when exposed to high relative humidity. The absence of any remarkable changes at low to moderate humidity levels is further evidence for the stability of this insulin formulation.

Figure 5:
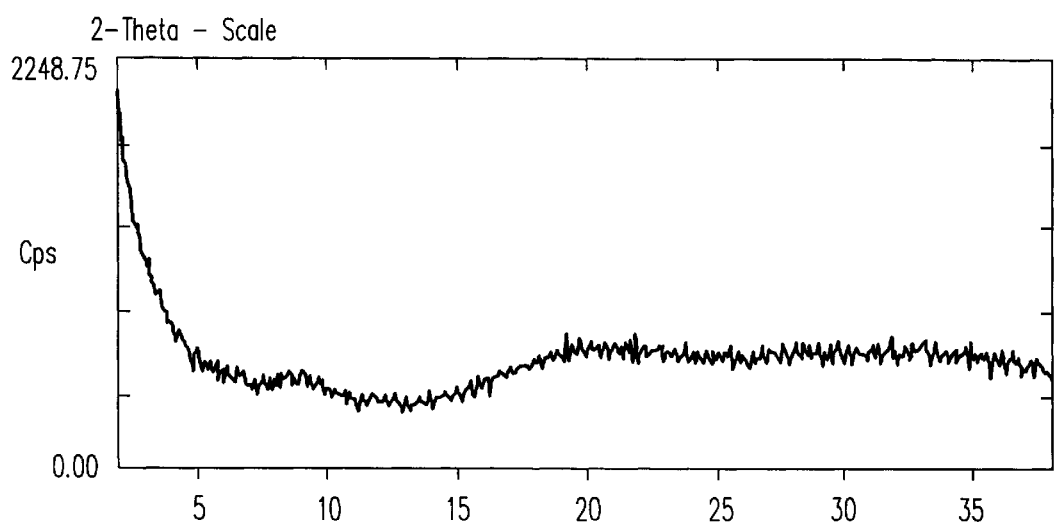
FIG. 5 shows an x-ray diffraction (XRD) pattern for a composition of this invention described in Example 2.
Figure 6:
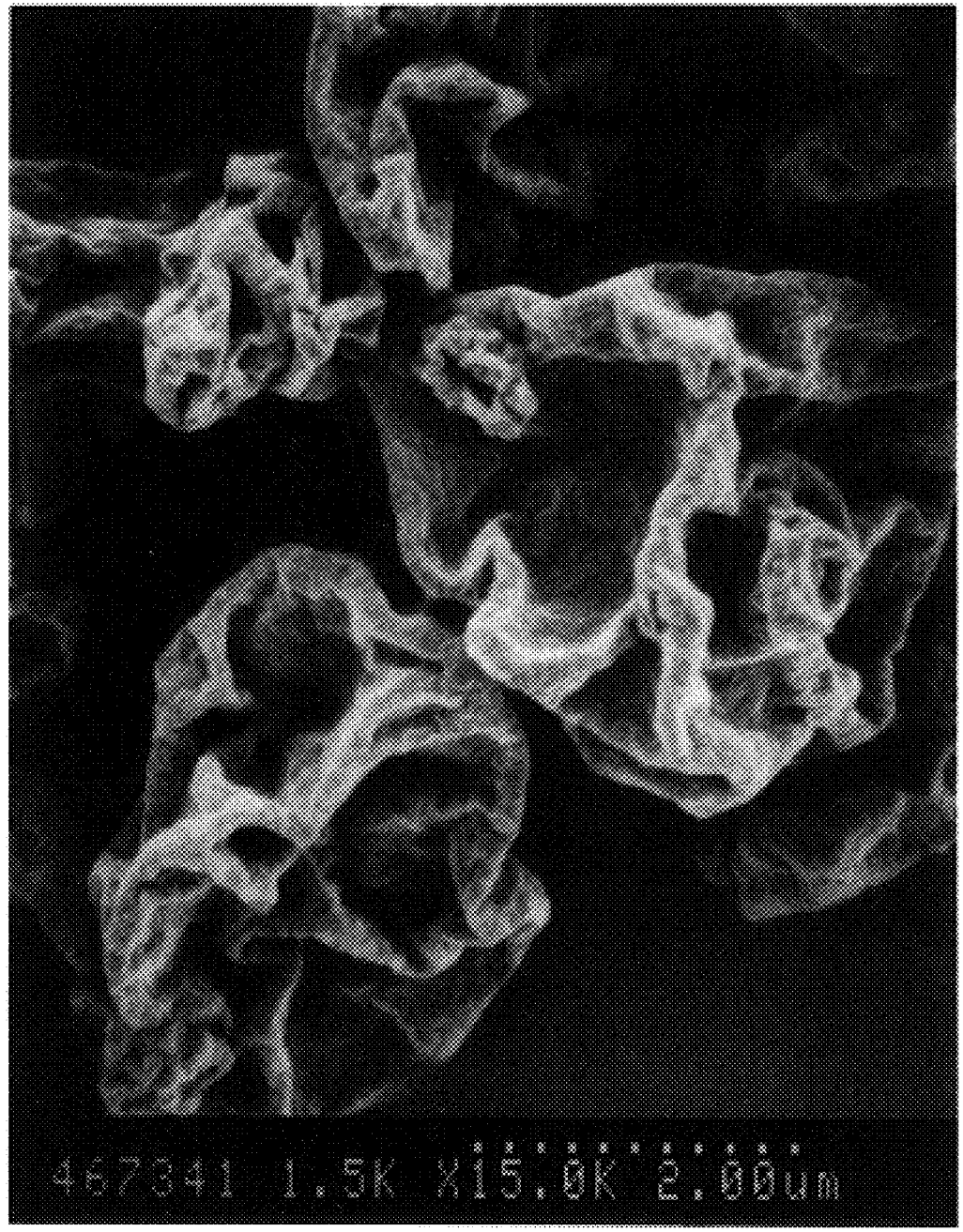
FIG. 6 shows a scanning electron microscope scanned image of illustrative particles of this invention.

Powders remained amorphous by X-ray diffraction analysis (FIG. 5) and polarizing light microscopy. Powder surface area, measured by nitrogen adsorption, ranged from 7 to 10 m2/g for these powders. The particles have a convoluted "raisin" structure scanning electron microscopy (SEM) analysis—FIG. 6) rather than a smooth spherical surface. (ESCA) surface chemistry analysis indicated that the particles contained a majority of the insulin on the surface of the particles. That is, ESCA analysis indicated that the surface composition was 52% insulin, 11% glycine, 16% mannitol, and 21% citrate while the overall formulation composition was 20% insulin, 2.6% glycine, 18% mannitol, and 59% citrate.

| Lot No. (Niro or Buchi) I-004 | Storage Temp (° C.) | Storage Time | % Del. Dose | MMAD (μm) | % particle mass <5 μm in size | % moisture | $T_g$ (° C.) |
|---|---|---|---|---|---|---|---|
| R95030 (Buchi) | 30 | Initial | 70 ± 4 | | | 1.7 | 90 |
| | | 4 wk | 71 ± 4 | | | 2.0 | |
| | | 12 wk | 73 ± 5 | | | 1.9 | |
| | cycled 2–37° C. | Initial | 70 ± 4 | | | 1.7 | 90 |
| | | 2 wk | 74 ± 4 | | | 2.0 | |
| | 40 | Initial | 70 ± 4 | | | 1.7 | 90 |
| | | 3–4 wk | 69 ± 4 | | | 2.0 | 89 |
| 96311 (Niro) | 30 | Initial | 73 ± 2 | 2.9 | 77 | 2.3 | 70 |
| | | 3 wk | 75 ± 7 | 2.5 | 85 | 2.0 | |
| | | 6 wk | 70 ± 7 | 2.1 | 89 | 3.1 | 77 |
| | | 12 wk | 68 ± 5 | 2.7 | 75 | 2.4 | 75 |
| | 40 | Initial | 73 ± 2 | 2.9 | 77 | 2.3 | 70 |
| | | 3 wk | 75 ± 5 | 2.4 | 85 | 1.9 | |
| | | 6 wk | 67 ± 5 | 2.9 | 74 | 2.5 | 72 |
| | | 12 wk | 71 ± 3 | 3.0 | 77 | 2.1 | 74 |
| | 40° C., 75% RH | Initial | 73 ± 4 | 2.8, 3.3 | 73, 83 | 2.3 | 70 |
| | | 1 wk | 73 ± 3 | 2.8, 2.8 | 76, 74 | 2.0 | 72 |
| | | 2 wk | 74 ± 2 | 3.2, 2.5 | 71, 82 | 2.3 | 71 |
| | | 3 wk | 69 ± 6 | 2.1, 2.3 | 91, 89 | 2.5 | 65 |
| | | 4 wk | 74 ± 2 | 1.5, 1.9 | 94, 92 | 2.9 | 63 |
| | | 6 wk | 72 ± 3 | 2.1, 2.6 | 87, 89 | 3.4 | 62 |

-continued

| Lot No. (Niro or Buchi) I-004 | Storage Temp (° C.) | Storage Time | % Del. Dose | MMAD (μm) | % particle mass <5 μm in size | % moisture | $T_g$ (° C.) |
|---|---|---|---|---|---|---|---|
| | 40° C. 95% RH Ambient Control | | | | | | |
| 95318 (Niro) | 30 | Initial | 82 ± 9 | 3.4 | 71 | 1.9 | 84 |
| | | 3 wk | 79 ± 6 | | | 2.2 | 82 |
| | | 6 wk | 89 ± 6 | | | 1.6 | 84 |
| | | 12 wk | 85 ± 6 | 3.3 | 69 | 2.0 | 84 |
| | | 25 wk | 78 ± 8 | 3.0 | 74 | 1.9 | 85 |
| | 40 | Initial | 82 ± 9 | 3.4 | 71 | 1.9 | 84 |
| | | 3 wk | 77 ± 5 | | | 2.2 | 84 |
| | cycled 2– | 12 wk | 86 ± 4 | | | 2.0 | 83 |
| | 37° C. | Initial | 82 ± 9 | 3.4 | 71 | 1.9 | 84 |
| | | 12 wk | 91 ± 5 | | | 1.9 | 82 |
| | 50 | Initial | 82 ± 9 | 3.4 | 71 | 1.9 | 84 |
| | | 12 wk | 81 ± 8 | | | | 84 |
| | | 25 wk | 81 ± 8 | 2.7 | 78 | | 88 |
| 95310 (Buchi) | 30 | Initial | 86 ± 4 | 2.9 | 76 | 1.7 | 88 |
| | | 3 wk | 81 ± 7 | 4.0 | 62 | 2.1 | 88 |
| | | 6 wk | 75 ± 4 | 3.9 | 62 | 1.8 | 88 |
| | | 12 wk | 77 ± 9 | 3.3 | 71 | 1.4 | 87 |
| | | 20 wk | 80 ± 6 | 2.8 | 74 | 1.4 | 89 |
| | | 12 month | 77 ± 5 | 3.9 | 62 | 1.4 | |
| | 40 | Initial | 86 ± 4 | 2.9 | 76 | 1.7 | 88 |
| | | 3 wk | 83 ± 3 | 4.0 | 68 | 1.7 | 89 |
| | | 6 wk | 78 ± 4 | 3.5 | 68 | 1.6 | 90 |
| | | 12 wk | 78 ± 8 | 3.0 | 73 | 1.6 | 91 |

Example 3

This example sets for a 60% Insulin composition that maintained protein integrity and aerosol stability after storage at 30° C., 40° C., 50° C., and temperature cycling at 2 to 37° C. ($T_g$-$T_s$>>30° C.).

A 60% insulin aerosol formulation was obtained by preparing a solution of human zinc insulin, mannitol, sodium citrate dihydrate, and citric acid monohydrate. Bulk crystalline human zinc insulin, obtained from Eli Lilly and Company, Indianapolis, Ind., and U.S.P. grade excipients were used. The solution contained 7.50 mg insulin, 1.27 mg mannitol, 3.38 mg sodium citrate, 0.026 mg sodium hydroxide, and 0.32 mg glycine per milliliter of deionized water for a total solids concentration of 12.5 mg/mL at pH 7.3.

A Niro Spray Dryer was used to prepare the dry powder using the following conditions:

| | |
|---|---|
| Temperature of aqueous solution | 2–8° C. |
| Atomizer chilling water return | 2–6° C. |
| Inlet temperature | 143–147° C. |
| Outlet temperature | 79–81° C. |
| Atomizer air flow | 12 scfm at 41–47 psig |
| Flow rate | 50 mL/min |

The dry powder (I-016) contained the following solids content:
60.0% insulin, 2.6% glycine, 27.1% sodium citrate, 10.1% mannitol, 0.2% sodium ion from sodium hydroxide Characterization and Stability Insulin powders were stored desiccated at <10% relative humidity (unless noted) at 30° C., 40° C., 50° C. and at temperature cycling conditions of 2 to 37° C. every 24 hours. Stability samples were evaluated for moisture content, aerosol performance based on delivered dose of insulin, and glass transition temperature using differential scanning calorimetry.

Thermal analysis using differential scanning calorimetry (DSC) and aerosol delivered dose testing were carried out as described previously. The aerosol particle size distribution was measured using a cascade impactor (California Measurements IMPAQ-6) connected to the device described for delivered dose testing.

Figure 7:
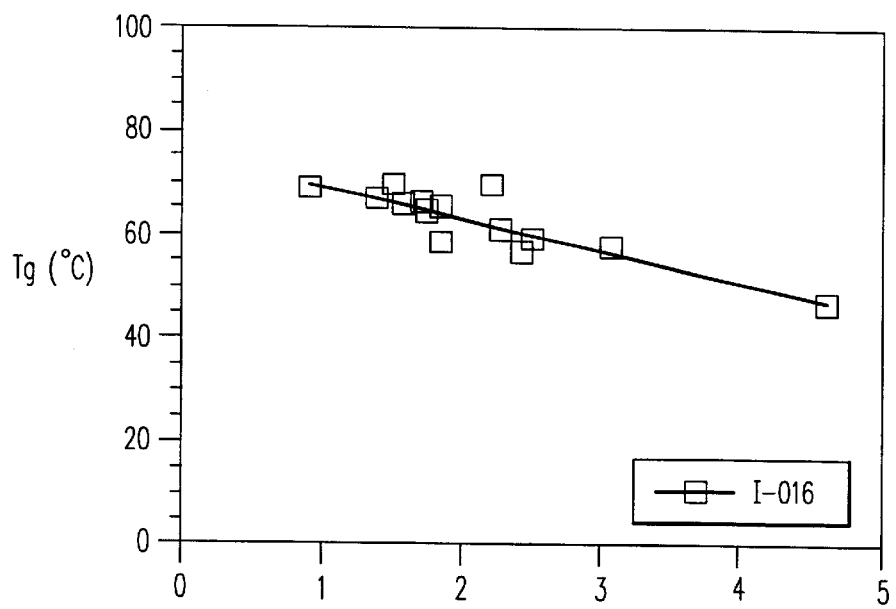
FIG. 7 is a graph illustrating the effect of moisture on the Tg of an illustrative composition of this invention.

Stability data are summarized below for several powders of this composition. Within the error of the measurements, the aerosol performance remained unchanged upon storage at dry conditions. This formulation was remarkable in the fact that the powder could take up to 4.6% moisture with out a loss of aerosol performance is presented in FIG. 7 showing that the $T_g$ is >40° C. up to about 5% moisture. Powders were amorphous by X-ray diffraction analysis. Powder surface area, measured by nitrogen adsorption, ranged from 7 to 10 m2/g for these powders. The particles have a convoluted "raisin" structure (SEM analysis) rather than a smooth spherical surface.

| Lot No. (I-016) | Storage Temp (° C.) | Storage Time | % Del. Dose | MMAD (μm) | % particle mass <5 μm in size | % moisture | $T_g$ (° C.) |
|---|---|---|---|---|---|---|---|
| 95322 | 30 | Initial | 95 ± 8 | 2.4 | 81 | 2.1 | 89 |
| | | 12 wk | 92 ± 7 | 2.3 | 81 | | 90 |
| | | 25 wk | 94 ± 6 | 3.2 | 72 | | 89 |
| | 40 | Initial | 95 ± 8 | 2.4 | 81 | 2.1 | 89 |
| | | 12 wk | 93 ± 6 | 2.2 | 81 | 1.0 | not done |
| | | 25 wk | 93 ± 5 | 2.6 | 76 | | 88 |
| | 50 | Initial | 95 ± 8 | 2.4 | 81 | 2.1 | 89 |
| | | 12 wk | 94 ± 7 | 2.2 | 85 | | 84 |
| | | 25 wk | 87 ± 6 | 2.8 | 74 | | 87 |
| 95322 after vacuum drying | 30 | Initial | 93 ± 8 | 2.7 | 76 | 1.4 | 95 |
| | | 12 wk | 96 ± 6 | 2.3 | 83 | 1.6 | 94 |
| | | 25 wk | 94 ± 6 | 2.8 | 73 | 1.6 | 82 |
| | 40 | Initial | 93 ± 8 | 2.7 | 76 | 1.4 | 95 |
| | | 12 wk | 93 ± 6 | | | 1.4 | 91 |
| | 50 | Initial | 93 ± 8 | 2.7 | 76 | 1.4 | 95 |
| | | 12 wk | 94 ± 6 | | | | 85 |
| | | 25 wk | 93 ± 6 | 3.2 | 72 | | 88 |
| 96317 | 30 | Initial | 87 ± 4 | 2.9, 3.1 | 77, 78 | 1.9 | 65 |
| | | 3 wk | 78 ± 4 | 2.7, 3.4 | 80, 72 | 2.0 | |
| | | 6 wk | 83 ± 3 | | | 2.2 | 64 |
| | 40° C., 75% RH | Initial | 87 ± 4 | 2.9, 3.1 | 77, 78 | 1.9 | 65 |
| | | 1 wk | 81 ± 3 | 2.3, 2.8 | 95, 80 | 2.1 | 59 |
| | | 2 wk | 84 ± 3 | 2.9, 2.8 | 73, 76 | 1.8 | 58 |
| | | 3 wk | 82 ± 3 | 2.9, 3.4 | 78, 74 | 2.4 | 63 |
| | | 4 wk | 81 ± 5 | 3.2, 3.2 | 74, 76 | 2.4 | 63 |
| | | 6 wk | 79 ± 4 | 2.8, 3.0 | 85, 79 | 3.0 | 57 |
| | | 7 wk | 69 ± 6 | | | 3.6 | |
| | Ambient Control | | | | | | |
| | Ambient Control | | | | | | |

Example 4

This example sets forth a 60% insulin composition that maintained protein integrity and aerosol stability after storage at 30° C., 40° C., 50° C., and temperature cycling at 2 to 37° C. ($T_g-T_s$=20 to 30° C.).

A 60% insulin aerosol formulation was obtained by preparing a solution of human zinc insulin, mannitol, sodium citrate dihydrate, and citric acid monohydrate. Bulk crystalline human zinc insulin, obtained from Eli Lilly and Company, Indianapolis, Ind., and U.S.P. grade excipients were used. The solution contained 7.50 mg insulin, 2.28 mg mannitol, 2.37 mg sodium citrate, 0.023 mg sodium hydroxide, and 0.32 mg glycine per milliliter of deionized water for a total solids concentration of 12.5 mg/mL at pH 7.3. Dry powders were prepared by spray-drying the aqueous solution using a Buchi Laboratory Spray Dryer under the following conditions:

| | |
|---|---|
| Temperature of aqueous solution | 2–8° C. |
| Inlet temperature | 128–130° C. |
| Outlet temperature | 85–88° C. |
| Feed rate | 5.0 mL/min |
| Jacketed cyclone temperature | 30–31° C. |

After all the aqueous solution was pumped into the spray dryer, the outlet temperature was maintained at 85° C. for 5 minutes by slowly decreasing the inlet temperature to provide a secondary drying.

A Niro Spray Dryer was also used to prepare dry powder using the following conditions:

| | |
|---|---|
| Temperature of aqueous solution | 2–8° C. |
| Atomizer chilling water return | 2–6° C. |
| Inlet temperature | 143–147° C. |
| Outlet temperature | 79–81° C. |
| Atomizer air flow | 12 scfm at 41–47 psig |
| Flowd rate | 50 mL/min |

The dry powder (I-005) contained the following solids content:
60.0% insulin, 2.6% glycine, 19.0% sodium citrate, 18.3% mannitol, 0.2% sodium ion from sodium hydroxide Characterization and Stability Insulin powders were stored desiccated at <10% relative humidity (unless noted) at 30° C., 40° C., 50° C. and at temperature cycling conditions of 2 to 37° C. every 24 hours. Stability samples were evaluated for moisture content, aerosol performance based on delivered dose of insulin, and glass transition temperature using differential scanning calorimetry.

Thermal analysis using differential scanning calorimetry (DSC) and aerosol delivered dose testing were carried out as described previously. The aerosol particle size distribution was measured using a cascade impactor (California Measurements IMPAQ-6) connected to the device described for delivered dose testing.

Stability data are summarized below for several powders of this composition. Within the error of the measurements, the aerosol performance remained unchanged upon storage.

Powders were amorphous by X-ray diffraction analysis. Powder surface area, measured by nitrogen adsorption, ranged from 7 to 10 m²/g for these powders. The particles have a convoluted "raisin" structure (SEM analysis) rather than a smooth spherical surface.

| Lot No. (I-005) | Storage Temp (° C.) | Storage Time | % Del. Dose | MMAD (μm) | % particle mass <5 μm in size | % moisture | $T_g$ (° C.) |
|---|---|---|---|---|---|---|---|
| 95317 (Buchi) | 30 | Initial | 86 ± 5 | 3.0 | 74 | 1.0 | 54 |
| | | 3 wk | 87 ± 6 | 2.7 | 75 | 1.4 | 50 |
| | | 6 wk | 89 ± 3 | 2.8 | 73 | 1.1 | 56 |
| | | 12 wk | 85 ± 7 | 3.1 | 72 | 0.5 | 51 |
| | | 20 wk | 92 ± 4 | 2.3 | 85 | 0.9 | 59 |
| | | 12 month | 87 ± 5 | 2.9 | 76 | | |
| | 40 | Initial | 86 ± 5 | 3.0 | 74 | 1.0 | 54 |
| | | 3 wk | 86 ± 8 | 3.0 | 72 | 0.8 | 58 |
| | | 6 wk | 89 ± 3 | 2.9 | 75 | 1.1 | 54 |
| | | 12 wk | 87 ± 7 | 2.2 | 83 | 0.5 | 48 |
| 95321 (Niro) | 30 | Initial | 95 ± 4 | 2.8 | 78 | 1.2 | 58 |
| | | 3 wk | 88 ± 3 | | | 1.7 | 43 |
| | | 6 wk | 96 ± 5 | | | 0.9 | 49 |
| | | 12 wk | 92 ± 5 | 2.4 | 82 | 1.2 | 54 |
| | | 25 wk | 91 ± 4 | 3.0 | 74 | 1.0 | 55 |
| | 40 | Initial | 95 ± 4 | 2.8 | 78 | 1.2 | 58 |
| | | 3 wk | 90 ± 6 | | | 1.1 | 55 |
| | | 6 wk | 94 ± 5 | | | 0.9 | 64 |
| | | 2 wk | 91 ± 6 | | | 1.1 | 66 |
| | 2–37 cycled | Initial | 95 ± 4 | 2.8 | 78 | 1.2 | 58 |
| | | 12 wk | 93 ± 5 | | | 1.1 | 52 |

Example 5

This example sets forth a 20% insulin composition that maintained protein integrity and aerosol stability after storage at 30° C., 40° C., and temperature cycled from 2 to 37° C. ($T_g-T_s>30°$ C.).

A 20% insulin aerosol formulation was obtained by preparing a solution of human zinc insulin, glycine, sodium citrate dihydrate, and citric acid monohydrate. Bulk crystalline human zinc insulin, obtained from Eli Lilly and Company, Indianapolis, Ind., and U.S.P. grade excipients were used. The solution contained 2.0 mg insulin, 7.73 mg sodium citrate, 0.01 mg citric acid, and 0.26 mg glycine per milliliter of deionized water for a total solids concentration of 10.0 mg/mL at pH 7.3. Dry powders were prepared by spray-drying the aqueous solution using a Buchi Laboratory Spray Dryer under the following conditions:

| | |
|---|---|
| Temperature of aqueous solution | 2–8° C. |
| Inlet temperature | 130° C. |
| Outlet temperature | 77° C. |
| Flow rate | 5.2 mL/min |
| Jacketed cyclone temperature | 30–31° C. |

After all the aqueous solution was pumped into the spray dryer, the outlet temperature was maintained at 80° C. for 1 minute by slowly decreasing the inlet temperature to provide a secondary drying.

Larger batches of powder were prepared by spray-drying a solution containing 2.5 mg insulin, 9.663 mg sodium citrate, 0.012 mg citric acid, and 0.325 mg glycine per milliliter of deionized water for a total solids concentration of 12.5 mg/mL at pH 7.3. A Niro Spray Dryer was used to prepare the dry powder using the following conditions:

| | |
|---|---|
| Temperature of aqueous solution | 2–8° C. |
| Atomizer chilling water return | 2–6° C. |
| Inlet temperature | 130° C. |
| Outlet temperature | 70° C. |
| Atomizer air flow | 12 scfm at 41–47 psig |
| Feed rate | 50 mL/min |

Both the Buchi and Niro dry powders (I-006) contained the following solids content:

20.0% insulin, 2.6% glycine, 77.3% sodium citrate, 0.1% citric acid

Characterization and Stability

Insulin powders were stored desiccated at <10% relative humidity at 30° C., 40° C., and at temperature cycling conditions of 2 to 37° C. every 24 hours. Stability samples were evaluated for moisture content, aerosol performance based on delivered dose of insulin, and glass transition temperature using differential scanning calorimetry.

Thermal analysis using differential scanning calorimetry (DSC) and aerosol delivered dose testing were carried out as described previously. The aerosol particle size distribution was measured using a cascade impactor (California Measurements IMPAQ-6) connected to the device described for delivered dose testing.

Stability data are summarized below for several powders of this composition prepared on both the Buchi and Niro spray dryers. Within the error of the measurements, the aerosol performance remained unchanged upon storage. Powders were amorphous by X-ray diffraction analysis and polarizing light microscopy. Powders exhibit very high $T_g$s (>100° C.) even at moisture contents ranging from 3 to 5%.

| Lot No. (Niro or Buchi) I-006 | Storage Temp (° C.) | Storage Time | % Del. Dose | MMAD (μm) | % particle mass <5 μm in size | % moisture | $T_g$ (° C.) |
| --- | --- | --- | --- | --- | --- | --- | --- |
| R95032 (Buchi) | 30 | Initial | 70 ± 3 | — | — | 3.2 | 107 |
| | | 4 wk | 70 ± 4 | | | 3.4 | |
| | | 12 wk | 76 ± 4 | | | 2.9 | |
| | cycled 2–37° C. | Initial | 70 ± 3 | — | — | 3.2 | 107 |
| | | 2 wk | 75 ± 4 | | | 3.9 | |
| | 40 | Initial | 70 ± 3 | — | — | 3.2 | 107 |
| | | 3–4 wk | 71 ± 5 | | | 4.6 | 106 |

Example 6

This example sets forth a 60% insulin composition that maintained protein integrity and aerosol stability after storage at 30° C., 40° C., and temperature cycling at 2 to 37° C. ($T_g$–$T_s$>30° C.)

A 60% insulin aerosol formulation was obtained by preparing a solution of human zinc insulin, glycine, sodium citrate dihydrate, and sodium hydroxide. Bulk crystalline human zinc insulin, obtained from Eli Lilly and Company, Indianapolis, Ind., and U.S.P. grade excipients were used. The solution contained 6.0 mg insulin, 3.71 mg sodium citrate, 0.026 mg sodium hydroxide, and 0.26 mg glycine per milliliter of deionized water for a total solids concentration of 10.0 mg/mL at pH 7.3. Dry powders were prepared by spray-drying the aqueous solution using a Buchi Laboratory Spray Dryer under the following conditions:

| | |
| --- | --- |
| Temperature of aqueous solution | 2–8° C. |
| Inlet temperature | 128–130° C. |
| Outlet temperature | 78° C. |
| Feed rate | 5.2 mL/min |
| Jacketed cyclone temperature | 30–31° C. |

After all the aqueous solution was pumped into the spray dryer, the outlet temperature was maintained at 78° C. for 5 minutes by slowly decreasing the inlet temperature to provide a secondary drying.

Dry powders (I-007) contained the following solids content:

60.0% insulin, 2.6% glycine, 37.1% sodium citrate, 0.3% sodium ion from sodium hydroxide Characterization and Stability Insulin powders were stored desiccated at <10% relative humidity at 30° C., 40° C., and at temperature cycling conditions of 2 to 37° C. every 24 hours. Stability samples were evaluated for moisture content, aerosol performance based on delivered dose of insulin, and glass transition temperature using differential scanning calorimetry.

Thermal analysis using differential scanning calorimetry (DSC) and aerosol delivered dose testing were carried out as described previously. The aerosol particle size distribution was measured using a cascade impactor (California Measurements IMPAQ-6) connected to the device described for delivered dose testing.

Stability data are summarized below for several powders of this composition prepared on both the Buchi and Niro spray dryers. Within the error of the measurements, the aerosol performance remained unchanged upon storage. Powders were amorphous by X-ray diffraction analysis and polarizing light microscopy. Powders exhibit very high $T_g$s (>100° C.). Citrate is an excellent glass former.

| Lot No. (Niro or Buchi) I-007 | Storage Temp (° C.) | Storage Time | % Del. Dose | MMAD (μm) | % particle mass <5 μm in size | % moisture | $T_g$ (° C.) |
| --- | --- | --- | --- | --- | --- | --- | --- |
| R95033 (Buchi) | 30 | Initial | 82 ± 3 | | | 2.1 | 115 |
| | | 4 wk | 80 ± 4 | | | 2.2 | |
| | | 12 wk | 81 ± 6 | | | 1.6 | |
| | cycled 2–37° C. | Initial | 82 ± 3 | | | 2.1 | 115 |
| | | 2 wk | 87 ± 3 | | | 1.8 | |
| | 40 | Initial | 82 ± 3 | | | 2.1 | 115 |
| | | 3–4 wk | 83 ± 5 | | | 1.8 | |

Example 7

This example sets forth a 20% insulin composition of this invention (a partially glassy, partially crystalline powder), which showed good aerosol stability at 30° C., 40° C., and 50° C. ($T_g$–$T_s$>>30° C.).

A 20% insulin aerosol formulation was obtained by preparing a solution of human zinc insulin, sucrose, sodium citrate dihydrate, glycine, and sodium hydroxide. Bulk crystalline human zinc insulin, obtained from Eli Lilly and Company, Indianapolis, Ind., and U.S.P. grade excipients were used. The solution contained 2.0 mg insulin, 4.74 mg sucrose, 3.00 mg sodium citrate, and 0.26 mg glycine per milliliter of deionized water for a total solids concentration of 10.0 mg/mL at pH 7.3. Dry powders were prepared by spray-drying the aqueous solution using a Buchi Laboratory Spray Dryer under the following conditions:

| | |
|---|---|
| Temperature of aqueous solution | 2–8° C. |
| Inlet temperature | 125° C. |
| Outlet temperature | 75° C. |
| Feed rate | 5.2 mL/min |
| Jacketed cyclone temperature | 30–31° C. |

After all the aqueous solution was pumped into the spray dryer, the outlet temperature was maintained at 78° C. for 5 minutes by slowly decreasing the inlet temperature to provide a secondary drying.

The dry powder (I-029) contained the following solids content:

20.0% insulin, 2.6% glycine, 30.0% sodium citrate, 47.2 sucrose, 0.2% sodium ion from sodium hydroxide Characterization and Stability Insulin powders were stored desiccated at <10% relative humidity (unless noted) at 30° C., 40° C., 50° C. and at temperature cycling conditions of 2 to 37° C. every 24 hours. Stability samples were evaluated for moisture content, aerosol performance based on delivered dose of insulin, and glass transition temperature using differential scanning calorimetry.

Thermal analysis using differential scanning calorimetry (DSC) and aerosol delivered dose testing were carried out as described previously. The aerosol particle size distribution was measured using a cascade impactor (California Measurements IMPAQ-6) connected to the device described for delivered dose testing.

Stability data are summarized below for several powders of this composition. Within the error of the measurements, the aerosol performance remained unchanged upon storage. Powders were predominantly glassy ($T_g$ of 98° C.) with some crystallinity observed by polarizing light microscopy.

Example 8

This example sets forth a 0.7% Interleukin-1 Receptor composition that maintained aerosol stability after storage at room temperature for 13 months.

Interleukin-1-receptor aerosol formulations were obtained by preparing solutions of human recombinant Interleukin-1 receptor (rhu IL-1R), tromethaminehydrochloride (TRIS HCl), tromethamine (TRIS), and raffinose pentahydrate. Human recombinant IL-1R, obtained from Immunex Corporation, Seattle, Wash., U.S.P. grade tromethamine, A.C.S. grade tromethamine hydrochloride, and GMP-qualified raffinose pentahydrate (Pfanstiehl, Waukegan, Ill.) were used. The 0.7% rhu IL-1 R formulation was achieved by combining 0.053 mg rhu IL-1R per 1.0 mL deionized water with 7.07 mg/mL raffinose and 0.373 mg/mL Tris buffer at pH 7.18.

A dry powder was prepared by spray-drying the aqueous solution using a Buchi Laboratory Spray Dryer under the following conditions:

| | |
|---|---|
| Temperature of aqueous solution | 2–8° C. |
| Inlet temperature | 135–137° C. |
| Outlet temperature | 92–93° C. |
| Feed rate | 4.9 mL/min |
| Jacketed cyclone temp | 30° C. |

After all the aqueous solution was pumped into the spray dryer, the outlet temperature was maintained at 90° C. for 15 minutes by slowly decreasing the inlet temperature to provide a secondary drying. The dry powder contained the following solids content:

0.7% rhu IL-1R, 94.3% raffinose, and 5.0% Tris buffer

Characterization and Stability

RHu IL-1R powders were stored desiccated at <10% relative humidity at 30° C. Stability samples were evaluated for moisture content, aerosol performance based on delivered dose and cascade impaction particle size distribution, and glass transition temperature using differential scanning calorimetry.

Thermal analysis using differential scanning calorimetry (DSC) and aerosol delivered dose testing were carried out as described previously. The aerosol particle size distribution was measured using a cascade impactor (California Measurements IMPAQ-6) connected to the device described for delivered dose testing.

| Lot No. (I-029) | Storage Temp (° C.) | Storage Time | % Del. Dose | MMAD ($\mu$m) | % particle mass <5 $\mu$m in size | % moisture | $T_g$ (° C.) |
|---|---|---|---|---|---|---|---|
| R95084 (Buchi) | 30 | Initial | 78 ± 6 | 2.9 | 74 | 1.2 | 98 |
| | | 6 wk | 76 ± 1 | | | | |
| | | 12 wk | 72 ± 4 | 2.6 | 80 | | |
| | 40 | Initial | 78 ± 6 | 2.9 | 74 | 1.2 | 98 |
| | | 12 wk | 74 ± 4 | | | | |

| Storage Temp (° C.) | Storage Time | % Del. Dose ± RSD | MMAD (μm) | % particle mass < 5 μm in size | % moisture | $T_g$ (° C.) |
|---|---|---|---|---|---|---|
| 30 | Initial | 53 ± 5 | 3.2 | 77 | 1.8 | 71 |
|  | 3 mo | 60 ± 15 | 3.0 | 76 | 1.6 |  |
|  | 6 mo | 61 ± 5 | 3.2 | 81 | 1.5 |  |
|  | 13 mo | 51 ± 7 | 2.7 | 86 | 0.9 |  |

Example 9

This example sets forth a 5.0% Interleukin-1 Receptor composition that maintained aerosol stability after storage at room temperature for 3 months.

Interleukin-1-receptor aerosol formulations were obtained by preparing solutions of human recombinant Interleukin-1 receptor (rhu IL-1R), tromethaminehydrochloride (TRIS HCl), tromethamine (TRIS), and raffinose pentahydrate. Human recombinant IL-1R, obtained from Immunex Corporation, Seattle, Wash., U.S.P. grade tromethamine, A.C.S. grade tromethamine hydrochloride, and GMP-qualified raffinose pentahydrate (Pfanstiehl, Waukegan, Ill.) were used. The 5.0% rhu IL-1 R formulation was achieved by combining 0.375 mg rhu IL-1R per 1.0 mL deionized water with 6.77 mg/mL raffinose and 0.351 mg/mL Tris buffer at pH 7.35.

A dry powder was prepared by spray-drying the aqueous solution using a Buchi Laboratory Spray Dryer under the following conditions:

| | |
|---|---|
| Temperature of aqueous solution | 2–8° C. |
| Inlet temperature | 138° C. |
| Outlet temperature | 91° C. |
| Feed rate | 4.9 mL/min |
| Jacketed cyclone temp | 30° C. |

After all the aqueous solution was pumped into the spray dryer, the outlet temperature was maintained at 90° C. for 15 minutes by slowly decreasing the inlet temperature to provide a secondary drying. The dry powder contained the following solids content:

5.0% rhu IL-1R, 90.3% raffinose, and 4.7% Tris buffer

Characterization and Stability

Rhu IL-1R powders were stored desiccated at <10% relative humidity at 30° C. Stability samples were evaluated for moisture content, aerosol performance based on delivered dose and cascade impaction particle size distribution, and glass transition temperature using differential scanning calorimetry.

Thermal analysis using differential scanning calorimetry (DSC) and aerosol delivered dose testing were carried out as described previously. The aerosol particle size distribution was measured using a cascade impactor (California Measurements IMPAQ-6) connected to the device described for delivered dose testing.

| Storage Temp (° C.) | Storage Time | % Del. Dose ± RSD | MMAD (μm) | % particle mass < 5 μm in size | % moisture | $T_g$ (° C.) |
|---|---|---|---|---|---|---|
| 30 | Initial | 49 ± 10 | 4.1 | 64 | 1.8 | 71 |
|  | 3 mo | 56 ± 7 | 3.5 | 77 | 2.1 |  |

Example 10

This example sets forth a 1.0% Interleukin-1 Receptor composition that maintained aerosol stability after storage at room temperature for 2.5 years at 30° C. and 47% RH Interleukin-1-receptor aerosol formulations were obtained by preparing solutions of human recombinant Interleukin-1 receptor (rhu IL-1R), tromethaminehydrochloride (TRIS HCl), tromethamine (TRIS), and raffinose pentahydrate. Human recombinant IL-1R, obtained from Immunex Corporation, Seattle, Wash., U.S.P. grade tromethamine, A.C.S. grade tromethamine hydrochloride, and GMP-qualified raffinose pentahydrate (Pfanstiehl, Waukegan, Ill.) were used. The 5.0% rhu IL-1 R formulation was achieved by combining 0.375 mg rhu IL-1R per 1.0 mL deionized water with 6.77 mg/mL raffinose and 0.351 mg/mL Tris buffer at pH 7.1.

A dry powder was prepared by spray-drying the aqueous solution using a Buchi Laboratory Spray Dryer under the following conditions:

| | |
|---|---|
| Temperature of aqueous solution | 2–8° C. |
| Inlet temperature | 140° C. |
| Outlet temperature | 90–92° C. |
| Feed rate | 5.3 mL/min |
| Jacketed cyclone temp | 30° C. |

After all the aqueous solution was pumped into the spray dryer, the outlet temperature was maintained at 90° C. for 15 minutes by slowly decreasing the inlet temperature to provide a secondary drying. The dry powder contained the following solids content:

1.0% rhu IL-1R, 94.3% raffinose, and 4.7% Tris buffer

Characterization and Stability

Rhu IL-1R powders were stored desiccated at approximately 47% relative humidity (using a chamber containing a saturated solution of potassium thiocyanate) at 30° C. Stability samples were evaluated for moisture content, aerosol performance based on delivered dose and cascade impaction particle size distribution, and glass transition temperature using differential scanning calorimetry.

Figure 14:
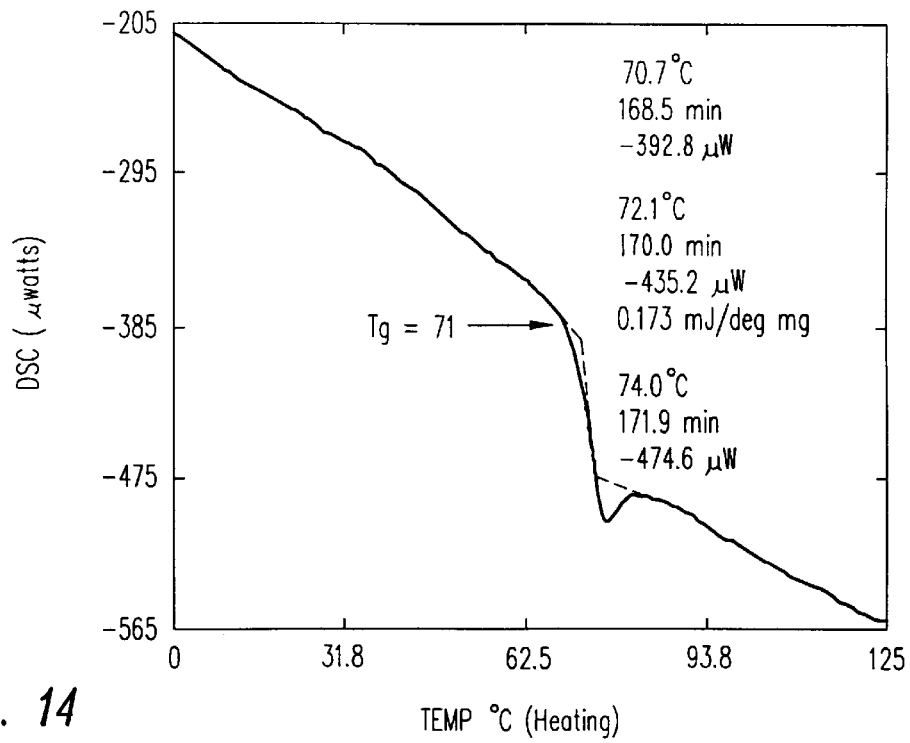
FIG. 14 shows a DSC thermogram of a composition of this invention.

Thermal analysis and aerosol delivered dose testing were carried out as described previously. A DSC scan showed a $T_g$ of 71° C. for the initial measurement (see FIG. 14). The aerosol particle size distribution was measured using a cascade impactor (California Measurements IMPAQ-6) connected to the device described for delivered dose testing. The aerosol data was collected using an early version of the device. The variability in the particle size data is probably not due to stability differences but rather variable performance of this powder in the early version of this device. The similarity in the data at 2 weeks and 2.5 years storage supports this conclusion, as well as the stability data presented in Example 8 for a similar powder.

| Storage Temp (° C.) | Storage Time | % Del. Dose ± RSD | MMAD (μm) | % particle mass < 5 μm in size | % moisture | $T_g$ (° C.) |
|---|---|---|---|---|---|---|
| 30°, 47% RH | Initial | 42 ± 5 | 3.0 | 83 | 1.6 | 71 |
| | 2 wk | 54 ± 12 | 3.9 | 66 | 1.7 | |
| | 6 wk | 54 ± 5 | 2.8 | 82 | 2.4 | |
| | 2.5 years | 52 ± 12 | 3.5 | 61 | 4.5 | |

Example 11

This example sets forth a 8.0% Interleukin-1 Receptor composition that maintained aerosol stability after storage at room temperature for 2.5 years at 30° C. and 47% RH.

Interleukin-1-receptor aerosol formulations were obtained by preparing solutions of human recombinant Interleukin-1 receptor (rhu IL-1R), tromethaminehydrochloride (TRIS HCl), tromethamine (TRIS), and raffinose pentahydrate. Human recombinant IL-1R, obtained from Immunex Corporation, Seattle, Wash., U.S.P. grade tromethamine, A.C.S. grade tromethamine hydrochloride, and GMP-qualified raffinose pentahydrate (Pfanstiehl, Waukegan, Ill.) were used. The 8.0% rhu IL-1 R formulation was achieved by combining 0.600 mg rhu IL-1R per 1.0 mL deionized water with 6.55 mg/mL raffinose and 0.351 mg/mL Tris buffer at pH 7.30.

A dry powder was prepared by spray-drying the aqueous solution using a Buchi Laboratory Spray Dryer under the following conditions:

| | |
|---|---|
| Temperature of aqueous solution | 2–8° C. |
| Inlet temperature | 142° C. |
| Outlet temperature | 91–92° C. |
| Feed rate | 5.3 mL/min |
| Jacketed cyclone temp | 30° C. |

After all the aqueous solution was pumped into the spray dryer, the outlet temperature was maintained at 90–92° C. for 15 minutes by slowly decreasing the inlet temperature to provide a secondary drying. The dry powder contained the following solids content:

8.0% rhu IL-1R, 87.3% raffinose, and 4.7% Tris buffer

Characterization and Stability

Rhu IL-1R powders were stored desiccated at approximately 47% relative humidity (using a chamber containing a saturated solution of potassium thiocyanate at 30° C.). Stability samples were evaluated for moisture content, aerosol performance based on delivered dose and cascade impaction particle size distribution, and glass transition temperature using differential scanning calorimetry or dielectric relaxation thermal analysis (DER).

Figure 8:
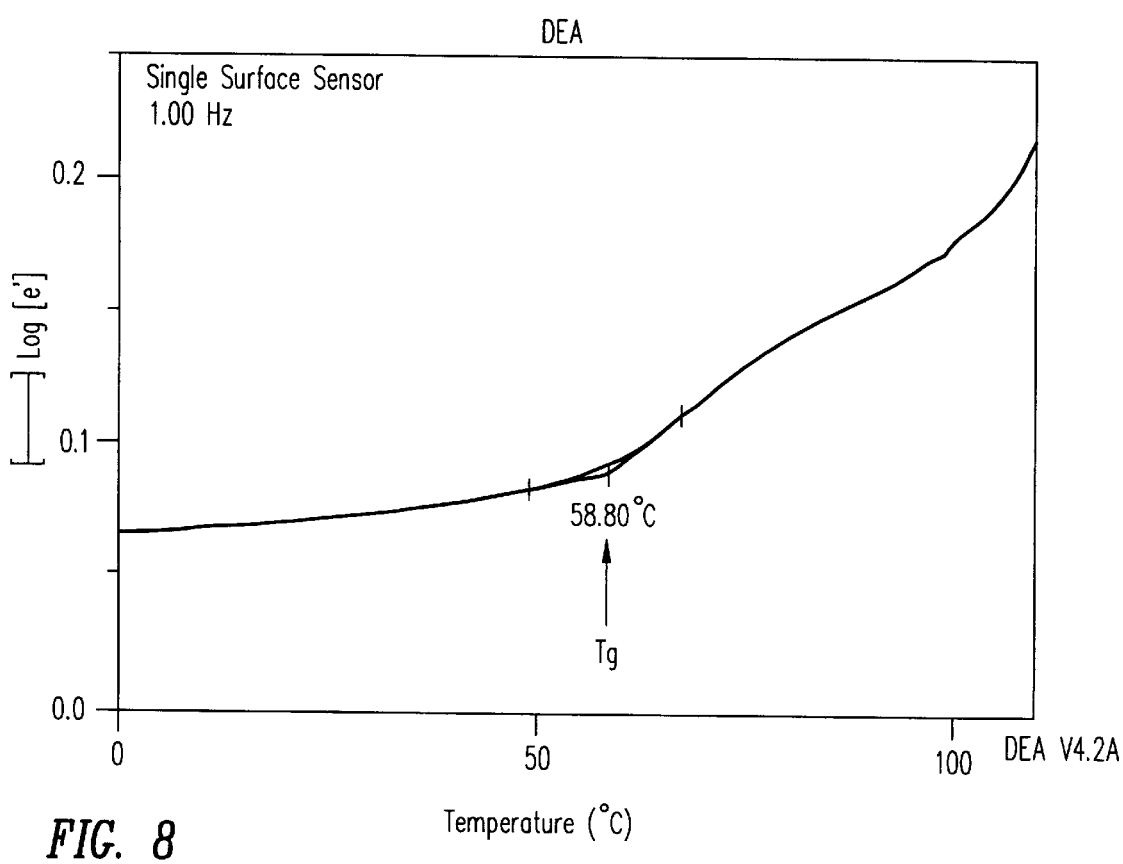
FIG. 8 sets forth a DER scan of a composition of this invention from about 0° C. to about 100° C. at a rate of about 1° C. per minute.
Figure 9A:
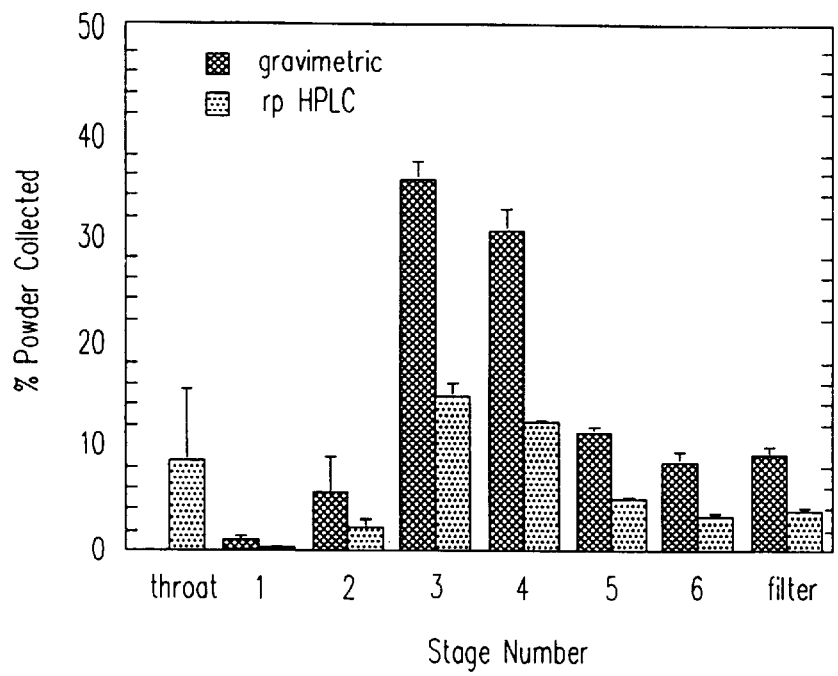
FIG. 9A provides a cascade impactor particle size distribution for a composition of this invention described in Example 11.
Figure 9B:
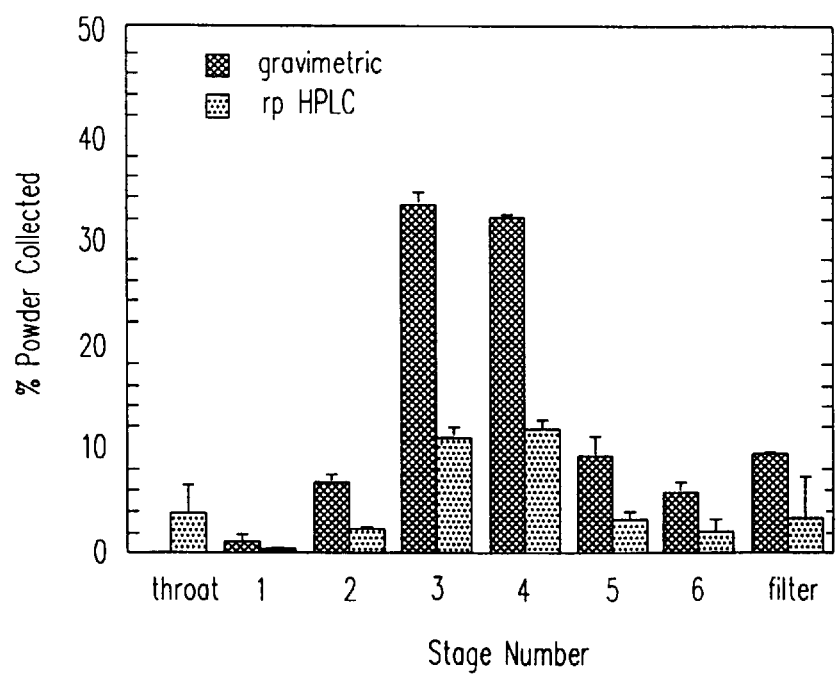
FIG. 9B shows a cascade impactor particle size distribution of an aged composition of this invention.

Thermal analysis using DER was accomplished using a dielectric thermal analyzer (Thermal Analysis Instruments) set up in a dry box at <5% relative humidity. FIG. 8 sets forth a DER scan from 0° C. to about 100° C. at 1° C./min. that was run on the formulation after 2.5 years. Here, as with the other DER analyses, the midpoint is used. The sample was supercooled to −70° C. and them scanned and data collected as the sample was warmed. Aerosol delivered dose testing was carried out as described previously. The aerosol particle size distribution was measured using a cascade impactor (California Measurements IMPAQ-6) connected to the device described for delivered dose testing. The 2.5 year storage results for delivered dose were remarkable because the powder had gained 2.x% moisture. The percent of the particle mass <5 μm may have decreased slightly or more likely was a result of the variability of this powder's performance in the early version of the device used for testing. The particle size distribution is shown in FIGS. 9A the initial timepoint and 9B after 2 weeks at 30° C. and 47% RH.

| Storage Temp (° C.) | Storage Time | % Del. Dose ± RSD | MMAD (μm) | % particle mass < 5 μm in size | % moisture | $T_g$ (° C.) |
|---|---|---|---|---|---|---|
| 30°, 47% RH | Initial | 47 ± 13 | 3.4 | 74 | 1.2 | 71 (DSC) |
| | 2 wk | 55 ± 11 | 3.3 | 72 | 1.2 | |
| | 6 wk | 43 ± 10 | 2.9 | 80 | 1.6 | |
| | 2.5 years | 49 ± 9 | 3.7 | 63 | 4.5 | 59 (DER) |

Example 12

This example sets forth a composition that maintained aerosol stability after storage for 11 months at 30° C.

The formulation was obtained by preparing solutions of tromethaminehydrochloride (TRIS HCl), tromethamine (TRIS), and raffinose pentahydrate (Pfanstiehl, Waukegan, Ill.). The raffinose/Tris formulation was achieved by combining 7.15 mg/mL raffinose and 0.351 mg/mL Tris buffer at pH 7.1.

A dry powder was prepared by spray-drying the aqueous solution using a Buchi Laboratory Spray Dryer under the following conditions:

| | |
|---|---|
| Temperature of aqueous solution | 2–8° C. |
| Inlet temperature | 118–120° C. |
| Outlet temperature | 81° C. |
| Feed rate | 5.8 mL/min |

The dry powder contained the following solids content:

95.3% raffinose, and 4.7% Tris buffer

Characterization and Stability

The raffinose/Tris powder was stored desiccated at 30° C. Stability samples were evaluated for moisture content, aerosol performance based on delivered dose and cascade impaction particle size distribution, and glass transition temperature using differential scanning calorimetry. Thermal analysis and aerosol delivered dose testing were carried out as described previously. The aerosol particle size distribution was measured using a cascade impactor (California Measurements IMPAQ-6) connected to the device described for delivered dose testing. Although the powder was a poor aerosol powder with only 26% delivered dose and a high relative standard deviation initially, the powder was stable for 11 months.

| Storage Temp (° C.) | Storage Time | % Del. Dose ± RSD | MMAD (μm) | % particle mass < 5 μm in size | % moisture | $T_g$ (° C.) |
|---|---|---|---|---|---|---|
| 30° | Initial | 26 ± 39 | 3.9 | 74 | 1.1 | 60 |
| | 3 month | 23 ± 7 | 2.8 | 72 | 0.7 | |
| | 6 month | 18 ± 9 | 2.6 | 79 | 0.7 | |
| | 11 month | 22 ± 14 | 3.5 | 53 | 0.5 | |

Example 13

This example sets forth 90% alpha-1 Antitrypsin composition showing stability for 13 months at ambient room temperature.

A 90% Alpha-1 Antitrypsin aerosol formulation was obtained by preparing a solution of purified human Alpha-1 Antitrypsin, sodium citrate dihydrate, and citric acid monohydrate. Bulk purified human Alpha-1 Antitrypsin solution in pH 6.0 sodium citrate buffer was obtained from Armour Pharmaceutical, Kangakee, Ill. A.C.S./U.S.P. grade excipients were used. The solution contained 4.99 mg human Alpha-1 Antitrypsin, 0.455 mg sodium citrate, 0.0.082 mg citric acid per milliliter of deionized water for a total solids concentration of 5.5 mg/mL at pH 6.0.

A dry powder was prepared by spray-drying the aqueous solution using a Buchi Laboratory Spray Dryer under the following conditions:

| | |
|---|---|
| Temperature of aqueous solution | 2–8° C. |
| Inlet temperature | 98–100° C. |
| Outlet temperature | 63–66° C. |
| Feed rate | 5.3 mL/min |
| Jacketed cyclone temp | 30° C. |

After all the aqueous solution was pumped into the spray dryer, the outlet temperature was maintained at 71–73° C. for 5 minutes by slowly decreasing the inlet temperature to provide a secondary drying. The dry powder was prepared to contain the following solids content:

90.3% rhu IL-1R and 9.7% citrate buffer

Characterization and Stability

Human Alpha-1 Antitrypsin powder was stored desiccated at <10% relative humidity (unless noted) at ambient room temperature. The initial UV spectrophotometric assay of the powder showed that the powder contained 82% alpha-1 antitrypsin in the solid, rather than the expected 90% concentration based on the bulk protein concentration. The human alpha-1 antitrypsin powder was reconstituted in water and analyzed for protein integrity by size exclusion and reversed phase chromatography, SDS-PAGE electrophoresis, and trpsyin chromogenic bioassay. The protein was undergraded by all methods. Powder stability samples were evaluated for moisture content, aerosol performance based on delivered dose of insulin, and glass transition temperature using dielectric thermal analysis.

Thermal analysis and aerosol delivered dose testing were carried out as described previously. A single $T_g$ at 40° C. followed by a softening or denaturation endotherm at about 160° C. was observed initially for this formulation by DSC analysis. At the end of study, thermal analysis was carried out by DER. DER showed a small change in dielectric constant at 39° C. and another $T_g$ with pronounced change in dielectric mobility at 93° C. The delivered dose was unchanged after 13 months storage.

Stability data are summarized below for several powders of this composition.

| Lot No. | Storage Temp (° C.) | Storage Time | % Del. Dose ± RSD | MMAD (μm) | % particle mass <5 μm in size | % moisture | $T_g$ (° C.) |
|---|---|---|---|---|---|---|---|
| 95011 | Ambient | Initial | 58 ± 4 | 1.3 | 90 | 3.9 | 40 |
| | | | 64 ± 3 | | | | |
| | | 3 month | 67 ± 8 | | | | |
| | | 4 month | 72 ± 3 | 1.7, 1.3 | 86, 90 | 2.8 | |
| | | 6 month | 73 ± 8 | | | | |
| | | 13 month | 62 ± 13 | | | 2.8, 2.3, 2.6 | 39, 93 (DER) |

Example 14

5% Human Serum Albumin showing aerosol stability for 6 months at 30° C., 40° C., and temperature cycled from 2 to 37° C.

A 5% human serum albumin aerosol formulation was obtained by preparing a solution of recombinant human serum albumin, mannitol, sodium citrate dihydrate, and citric acid monohydrate. Bulk human serum albumin solution was obtained from Miles Inc., Kankakee, Ill. (Pentex Fr V, Low Endotoxin, Fatty Acid Free). A.C.S./U.S.P. grade excipients were used. The solution contained 1.25 mg human serum albumin, 20.30 mg mannitol, 3.28 mg sodium citrate, 0.17 mg citric acid per milliliter of deionized water for a total solids concentration of 25.0 mg/mL at pH 6.6.

A Niro Spray Dryer was used to prepare the dry powder using the following conditions:

| | |
|---|---|
| Temperature of aqueous solution | 2–8° C. |
| Atomizer chilling water return | 2–6° C. |
| Inlet temperature | 120° C. |
| Outlet temperature | 60.5–62.8° C. |
| Atomizer air flow | 11–12 scfm at 43 psig |
| Solution feed rate | 50 mL/min |

The dry powder was prepared to contain the following solids content:

5.0% human serum albumin, 81.1% mannitol, and 13.8% citrate buffer

Characterization and Stability

Figure 10:
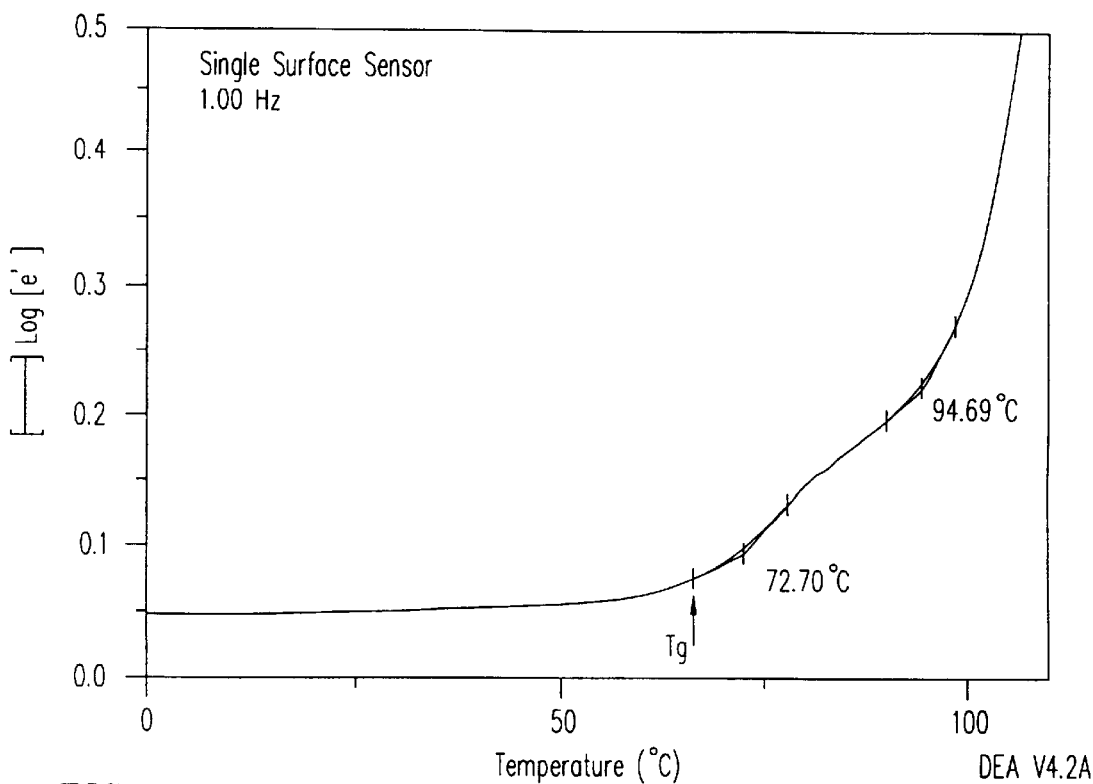
FIG. 10 shows a DER (dielectric relaxation) scan thermogram of a composition of this invention.

Human serum albumin powder was stored desiccated at <10% relative humidity at 30° C. and 40° C. Powder stability samples were evaluated for moisture content, aerosol performance based on delivered dose, polarizing light microscopy, and glass transition temperature using DER. (See FIG. 10).

Thermal analysis and aerosol delivered dose testing were carried out as described previously. The aerosol particle size distribution was measured using a cascade impactor (Anderson model) connected to the device described for delivered dose testing. The powder contained a significant amount of crystallinity by polarizing light microscopy (estimated to be at least half of the particle mass). Thermal analysis showed that the amorphous phase had a glass transition temperature of 73° C. Aerosol performance was consistent over the 6 months storage.

Stability data are summarized below for several powders of this composition.

The powder was sifted through a 35 mesh sieve after spray drying and before filling into blister packs at 5 mg per pack.

Characterization and Stability

Albuterol powder was stored desiccated at <10% relative humidity at 30° C., 40° C., and temperature cycling from 2 to 40° C. at 12 hour cycle intervals. Powder stability samples were evaluated for moisture content, aerosol performance based on delivered dose, polarizing light microscopy, moisture isotherm analysis and glass transition temperature using DSC.

Thermal analysis and aerosol delivered dose testing were carried out as described previously, with a DSC scan rate of

| Lot No. | Storage Temp (° C.) | Storage Time | % Del. Dose ± RSD | MMAD (μm) | % particle mass <5 μm in size | % moisture | $T_g$ (° C.) |
|---|---|---|---|---|---|---|---|
| NR9508 | 30 | Initial | 53 ± 4 | | | 1.2 | |
| | | 3 month | 59 ± 5 | | | | |
| | | 6 month | 51 ± 6 | | | | |
| | cycled 2–37° C. | Initial | 53 ± 4 | | | 1.2 | |
| | 40 | 3 month | 57 ± 5 | | | | |
| | | 6 month | 51 ± 6 | | | | |
| | | Initial | 53 ± 4 | | | 1.2 | |
| | | 3 month | 60 ± 4 | | | | |
| | | 6 month | 50 ± 8 | | | | 73 (DER) |

Example 15

This example sets forth a 2% albuterol composition (lot AS024) showing aerosol stability for 6 weeks at 30° C., 40° C., and temperature cycled from 2 to 40° C.

A 2.3% Albuterol sulfate (ie, 2% albuterol) formulation was obtained by preparing a solution of albuterol sulfate and lactose. Bulk albuterol sulfate was obtained from Profarmaco (Milano, Italy). U.S.P. grade lactose was used. The solution contained 0.60 mg albuterol sulfate and 25.68 mg lactose per milliliter of deionized water for a total solids concentration of 26.28 mg/mL at a pH of 4.6.

A Niro Spray Dryer was used to prepare the dry powder using the following conditions:

| | |
|---|---|
| Temperature of aqueous solution | 2–8° C. |
| Atomizer chilling water return | 2–6° C. |
| Inlet temperature | 120° C. |
| Outlet temperature | 64.7–67.2° C. |
| Atomizer air flow | 12 scfm at 43 psig |
| Solution feed rate | 50 mL/min |

The dry powder was prepared to contain the following solids content: 2.3% albuterol sulfate and 97.7% lactose.

2.5° C./minutes instead of 1° C./minute. The aerosol particle size distribution was measured using a cascade impactor (California Measurements) connected to the device described for delivered dose testing. The powder was amorphous by polarizing light microscopy. Thermal analysis showed a $T_g$ of 83° C. Aerosol performance was consistent over 6 weeks storage.

Figure 11:
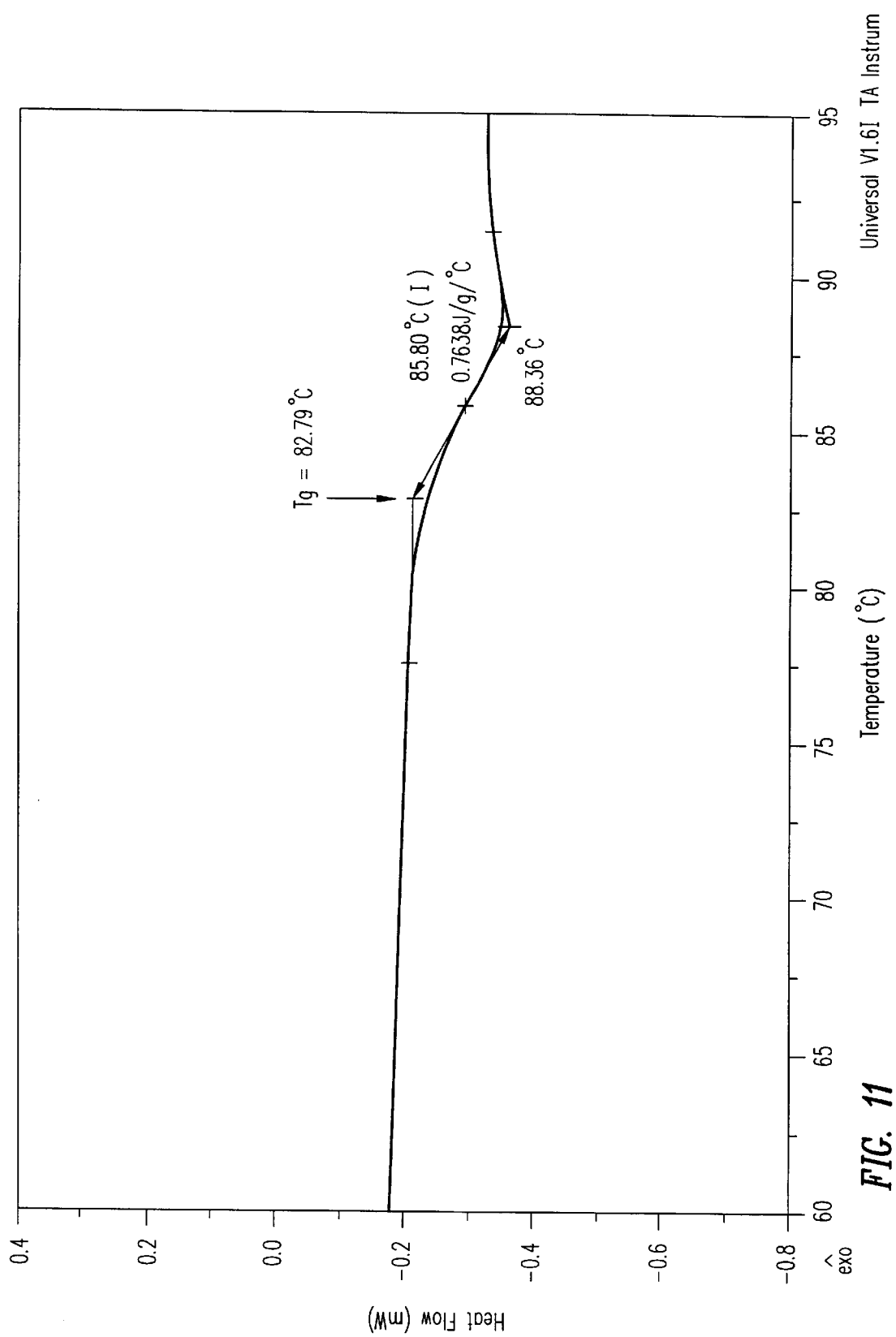
FIG. 11 shows a DSC thermogram of a composition of this invention.
Figure 12:
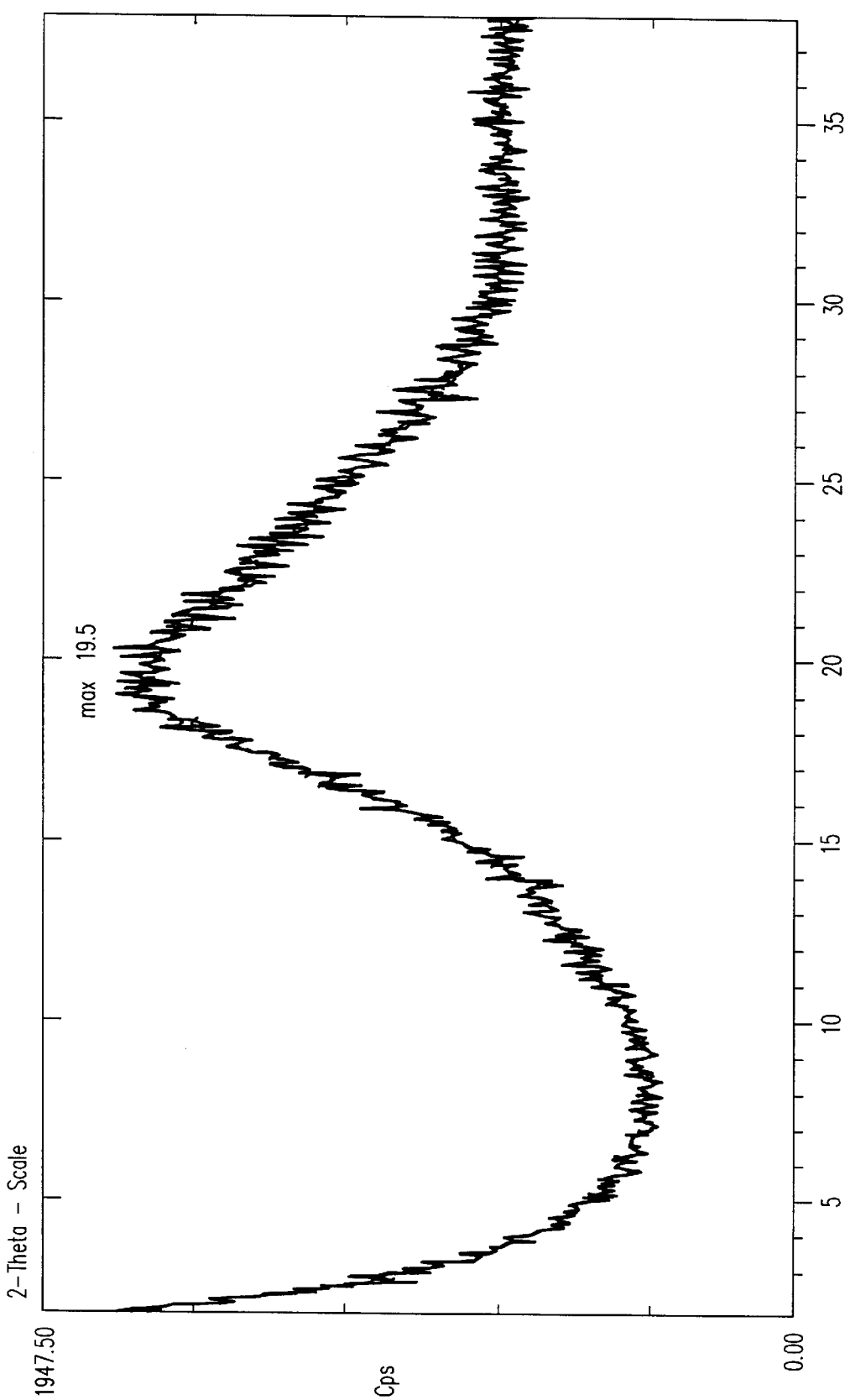
FIG. 12 is an x-ray diffraction pattern of a composition of this invention.

The 2% albuterol lactose powder was amorphous by polarizing light microscopy, DSC, and X-Ray diffraction analysis. A DSC plot is given in FIG. 11 showing the glass transition temperature of 83° C. The X-Ray diffraction pattern, shown in FIG. 12, has a broad halo pattern which corresponds to low angle order in the material and is characteristic of a glassy amorphous material.

Figure 13:
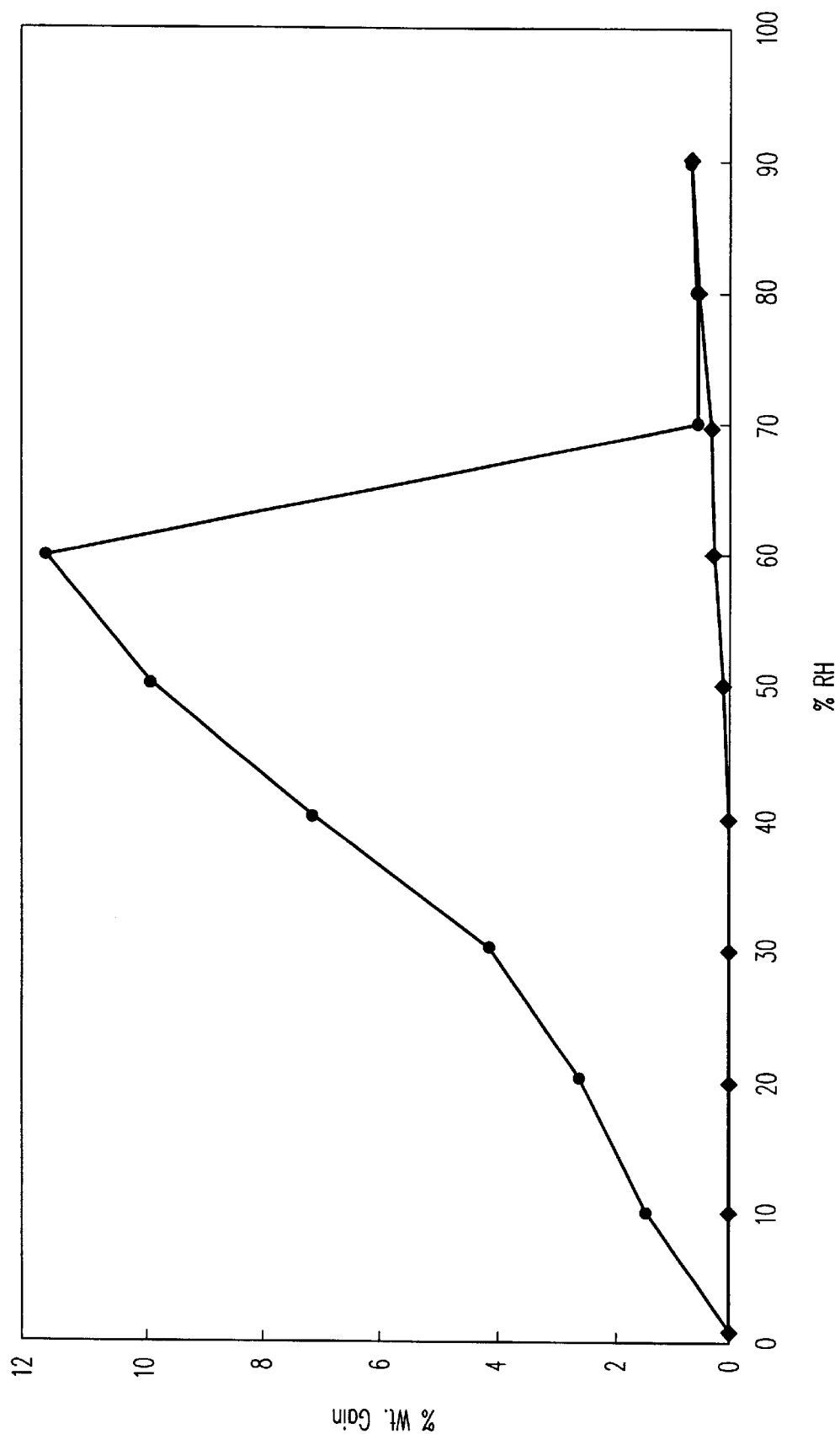
FIG. 13 shows a moisture sorption isotherm of a composition of this invention.

As a material is plasticized by increasing moisture content, the $T_g$ decreases (as well as $T_g-T_s$) and the potential for crystallization increases. This is demonstrated by the moisture sorption isotherm at 25° C. shown in FIG. 13. For the 2% albuterol/lactose formulation, the moisture uptake increases with humidity until 60% relative humidity is reached, where there is a sharp decrease in weight gain as the lactors monohydrate crystal is formed. At this point, the powder converted from amorphous to crystalline, which was confirmed by polarizing light microscopy before and after the moisture sorption experiment. The changes in solid state for this powder occurred at relative humidities that are significantly higher than the desiccated storage condition for the powder.

Stability data are summarized below for several powders of this composition.

| Lot No. | Storage Temp (° C.) | Storage Time | % Del. Dose ± RSD | MMAD (μm) | % particle mass <5 μm in size | % moisture | $T_g$ (° C.) |
|---|---|---|---|---|---|---|---|
| AS024 | 30 | Initial | 55 ± 6 | 3.6, 3.0 | 62, 74 | 2.3 | 83 |
| | | 3 wk | 51 ± 12 | 3.5, 3.6 | 63, 63 | | |
| | | 6 wk | 52 ± 12 | 3.7, 3.0 | 61, 74 | | |
| | cycled 2–40° C. | Initial | 55 ± 6 | 3.6, 3.0 | 62, 74 | 2.3 | |
| | | 3 wk | 52 ± 7 | 3.8, 4.4 | 60, 54 | | |
| | | 6 wk | 55 ± 8 | 3.1, 4.0 | 71, 60 | | |
| | 40 | Initial | 55 ± 6 | 3.6, 3.0 | 62, 74 | 2.3 | |
| | | 3 wk | 52 ± 8 | 4.6, 3.9 | 54, 60 | | |
| | | 6 wk | 55 ± 10 | 3.7, 4.2 | 62, 58 | | |

Example 16

This example sets forth a 5% albuterol composition showing aerosol stability for 6 weeks at 30° C., 40° C., and temperature cycled from 2 to 40° C. for 12 hour cycle intervals A 5.7% Albuterol sulfate (5% albuterol) formulation was obtained by preparing a solution of albuterol sulfate and lactose. Bulk albuterol sulfate was obtained from Profarmaco (Milano, Italy). U.S.P. grade lactose was used. The solution contained 1.50 mg albuterol sulfate and 24.74 mg lactose per milliliter of deionized water for a total solids concentration of 26.24 mg/ML at a pH of 4.7.

A Niro Spray Dryer was used to prepare the dry powder using the following conditions:

| | |
|---|---|
| Temperature of aqueous solution | 2–8° C. |
| Atomizer chilling water return | 2–6° C. |
| Inlet temperature | 115° C. |
| Outlet temperature | 62° C. |
| Atomizer air flow | 12 scfm at 43 psig |
| Solution feed rate | 55 mL/min |

The dry powder was prepared to contain the following solids content: 5.7% albuterol sulfate and 94.3% lactose. The powder was sifted through a 35 mesh sieve after spray drying and before filling into blister packs at 5 mg per pack.

Characterization of Stability

Albuterol powder was stored desiccated at <10% relative humidity at 30° C., 40° C., and temperature cycling from 2 to 40° C. at 12 hour cycle intervals. Powder stability samples were evaluated for moisture content, aerosol performance based on delivered dose, polarizing light microscopy, moisture isotherm analysis and glass transition temperature using DSC.

Thermal analysis and aerosol delivered dose testing were carried out as described previously. The aerosol particle size distribution was measured using a cascade impactor (California Measurements) connected to the device described for delivered dose testing. The powder was amorphous by polarizing light microscopy. Thermal analysis showed a $T_g$ of 95° C. Aerosol performance was consistent over 12 weeks storage.

Stability data are summarized below for several powders of this composition.

| Lot No. | Storage Temp (° C.) | Storage Time | % Del. Dose ± RSD | MMAD (μm) | % particle mass <5 μm in size | % moisture | $T_g$ (° C.) |
|---|---|---|---|---|---|---|---|
| AS020 | 30 | Initial | 50 ± 13 | 2.5, 2.2 | 83, 90 | 2.6 | 95 |
| | | 6 wk | 43 ± 15 | 3.4, 2.7 | 71, 80 | | |
| | | 12 wk | 43 ± 9 | 3.7, 3.0 | 69, 64 | | |
| | 40 | Initial | 50 ± 13 | 2.5, 2.2 | 83, 90 | 2.6 | |
| | | 6 wk | 50 ± 8 | 2.6, 2.8 | 82, 81 | | |
| | | 12 wk | 43 ± 16 | 2.9 | 92, 77 | | |

Example 17

This example sets forth a 3.0% Salmon Calcitonin composition that maintained aerosol stability after storage at room temperature for 8 weeks Salmon calcitonin (MW 3431) aerosol formulations was obtained by preparing solutions of salmon calcitonin, mannitol, sodium citrate dihydrate, and citric acid monohydrate. Salmon calcitonin, obtained from Bachem, Torrance, Calif., U.S.P. grade excipients were used. The 3.0% salmon calcitonin solution was achieved by combining 0.225 mg salmon calcitonin per 1.0 mL deionized water with 0.75 mg/mL mannitol, 3.88 mg/mL sodium citrate and 2.64 mg/mL citric acid at pH 4.5.

A dry powder was prepared by spray-drying the aqueous solution using a Buchi Laboratory Spray Dryer under the following conditions:

| Temperature of aqueous solution | 2–8° C. |
|---|---|
| Inlet temperature | 130° C. |
| Outlet temperature | 76° C. |
| Feed rate | 5.0 mL/min |
| Jacketed cyclone temp | 30° C. |

After all the aqueous solution was pumped into the spray dryer, the outlet temperature was maintained at 75–77° C. for 10 minutes by slowly decreasing the inlet temperature to provide a secondary drying. The dry powder contained the following solids content 3.0% salmon calcitonin, 10.0% mannitol, 51.7% sodium citrate, and 35.3% citric acid Characterization and Stability Salmon powders were stored desiccated at <10% relative humidity at ambient room temperature, 30° C., 40° C., and 80° C. Stability samples were evaluated for moisture content, aerosol performance based on delivered dose and cascade impaction particle size distribution, and glass transition temperature using differential scanning calorimetry.

Thermal analysis using differential scanning calorimetry (DSC) was carried out as described previously except that a scan rate of 2.5° C./minute was used. The aerosol particle size distribution was measured using a cascade impactor (California Measurements IMPAQ-6) connected to the device described for delivered dose testing. Aerosol and DSC data are shown below. DSC thermograms of the 40° C. stability study are shown in Figure X. A plot of $T_g$ versus moisture content for the powders is shown in Figure X. The glass transition temperature, moisture content, and aerosol results were consistent over the 8 week period at 40° C. The powder showed stable aerosol performance when stored below the $T_g$ and even above the $T_g$ for 4 hours at 80° C. However, after aging the powder for 8 hours at 80° C., the delivered dose efficiency declined, as would be expected for storage 10° C. above the glass transition temperature. The chemical stability of salmon calcitonin in the powder, in contrast, was stable after 8 hours at 80° C. Reverse phase HPLC showed no changes in purity of the drug while physical stability was more sensitive to the difference in storage temperature and $T_g$.

| Storage Temp (° C.) | Storage Time | % Del. Dose | % moisture | $T_g$ (° C.) |
|---|---|---|---|---|
| Ambient RT | Initial | 63 ± 5 | 0.9 | 68 |
| | 14 wks | 60 ± 5 | 0.8 | 71 |
| 30 | 4 wks | 59 ± 6 | 1.2 | |
| | 8 wks | 58 ± 6 | 1.0 | 68 |
| 40 | 4 wks | 56 ± 8 | 1.6 | |
| | 8 wks | 57 ± 4 | 1.0 | 72 |
| 80 | 4 hours | 59 ± 5 | | |
| | 8 hours | 28 ± 3 | | |

Example 18

This example sets forth 0.34% elcatonin compositions

Three formulations of elcatonin were prepared by spray drying.

Elcatonin powder formulations were obtained by preparing solutions of elcatonin and glass formers and additives. Elcatonin was obtained from Asahi Chemicat Industry Company, Ltd. (Tokyo, Japan). U.S.P. grade povidone (PVP K-15 from ISP Technologies, Wayne, N.J.) and sodium citrate was used. Pectin was reagent grade (Sigma).

The 0.34% elcatonin/70% povidone/30% citrate solution was achieved by combining 25.5 µg elcatonin per 1.0 mL deionized water with 5.25 mg/mL PVP K-15, and 2.25 sodium citrate buffer at pH 5.5. The 0.34% elcatonin/90% povidone/10% citrate solution was achieved by combining 25.5 µg elcatonin per 1.0 mL deionized water with 6.75 mg/mL PVP K-15, and 0.75 mg/mL sodium citrate buffer at pH 5.5. Dry powders were prepared by spray-drying the aqueous solution using a Buchi Laboratory Spray Dryer under the following conditions:

| Temperature of aqueous solution | 2–8° C. |
|---|---|
| Inlet temperature | 140° C. |
| Outlet temperature | 88° C. |
| Feed rate | 5.0 mL/min |
| Jacketed cyclone temp | 30° C. |

After all the aqueous solution was pumped into the spray dryer, the outlet temperature was maintained at 88° C. for 5 minutes by slowly decreasing the inlet temperature to provide a secondary drying.

The 0.34% elcatonin/50% povidone/50% citrate solution was achieved by combining 25.5 µg elcatonin per 1.0 mL deionized water with 3.75 mg/mL pectin, and 3.75 mg/mL sodium citrate buffer at pH 5.5. A dry powder was prepared by spray-drying the aqueous solution using a Buchi Laboratory Spray Dryer under the following conditions:

| Temperature of aqueous solution | 2–8° C. |
|---|---|
| Inlet temperature | 125° C. |
| Outlet temperature | 76° C. |
| Feed rate | 5.0 mL/min |
| Jacketed cyclone temp | 30° C. |

Characterization

Elcatonin powders were analyzed by aerosol testing, dielectric thermal analysis, and moisture content as described previously. The powders were suspended and dispersed in a hexade mixture (Sedisperse, Micromeritics) and analyzed for primary particle size distribution by centrifugal sedimentation using an Horiba Particle Size Analyzer.

The powders look promising with suitably high $T_g$ for powder stability and initial aerosol delivered dose greater than 50%. Results are shown in the table.

| Formulation | Mass Median Diamer (Horiba) | % < 5 µM (Horiba) | Del. Dose (%) | Moisture Content (%) | $T_g$ (DER) |
|---|---|---|---|---|---|
| 0.3% elcatonin/ 70% PVP/30% citrate | 1.6 | 89 | 53 ± 16 | 0.9 | 48 |
| 0.3% elcatonin/ 90% PVP/10% citrate | 2.1 | 100 | 59 ± 4 | 1.1 | 47 |
| 0.3% elcatonin/ 50% pectin/50% citrate | 2.1 | 95 | 51 ± 10 | 2.1 | 57 |

What is claimed is:

1. An aerosolized powder composition for pulmonary administration that, prior to aerosolization, has been stored for a minimum period of 3 weeks at a storage temperature ($T_s$) that is at least 10° C. lower than the glass transition temperature ($T_g$) of said composition, said composition comprising a pharmaceutically-acceptable glassy matrix and a pharmacologically active material within the glassy matrix, and characterized by an MMAD between about 1–5 microns both before and after storage.

2. The composition of claim 1, wherein the difference between $T_g$ and $T_s$ is at least about 20° C.

3. The composition of claim 1, wherein the difference between $T_g$ and $T_s$ is at least about 30° C.

4. The composition of claim 1, wherein the $T_g$ is about 35° C. to about 200° C.

5. The composition of claim 4, wherein the $T_g$ is greater than about 45° C.

6. The composition of claim 5, wherein the $T_g$ is greater than about 55° C.

7. The composition of claim 1, wherein $T_s$ is about 2° C. to about 30° C. and $T_g$ is about 22° C. to about 200° C.

8. The composition of claim 1, wherein the glassy matrix comprises a glass former selected from the group consisting of carbohydrates, carbohydrate derivatives, carbohydrate polymers, organic carboxylic acid salts, synthetic organic polymers, proteins, peptides, amino acids and polyamino acids.

9. The composition of claim 1, wherein the glass former is selected from the group consisting of sodium citrate, raffinose, lactose, trehalose, maltotriose, maltodextrin, maltose, glucopyranosyl-sorbitol, glucopyranosyl-mannitol, polydextrose, sucrose, cycloclodextrin, casein, HSA, hydroxyethyl starch, stachyose, magnesium gluconate, and celloboise.

10. The composition of claim 9, wherein the glass former is selected from the group consisting of sodium citrate, raffinose, lactose, trehalose, maltodextrin, maltose, sucrose, stachyose, magnesium gluconate, and gluocopyranosyl-mannitol.

11. The composition of claim 1, which prior to aerosolization, is in unit dosage form.

12. The combination of claim 11, wherein the unit dosage form includes a moisture barrier.

13. The composition of claim 1, aerosolized in a current of air.

14. A process for maintaining the aerosol performance of a powder composition over time, said process comprising:

(a) removing solvent from a solution comprising a solvent, a glass former and a pharmacologically active material under conditions effective to form a glassy matrix composition suitable for pulmonary administration, said composition having (i) the pharmacologically active material within the matrix, (ii) a glass transition temperature ($T_g$), and (iii) an MMAD from 1–5 microns, and (b) storing the composition at a storage temperature ($T_s$) that is at least 10° C. lower than said $T_g$, such that the composition maintains an MMAD from 1–5 microns when stored at said $T_s$ for a minimum period of 3 weeks, and (c) aerosolizing said composition.

15. The process of claim 14, wherein the solvent is removed by spray drying.

16. The process of claim 14, wherein the solvent is removed by evaporative drying.

17. The process of claim 14, wherein the solvent is removed by chemical precipitation.

18. The process of claim 14, wherein the solvent is water.

19. The process of claim 14, wherein the solvent is ethanol.

20. The process of claim 14, wherein the difference between $T_g$ and $T_s$ is at least about 20° C.

21. The process of claim 20 wherein the difference between $T_g$ and $T_s$ is at least about 30° C.

22. The process of claim 14, wherein the $T_g$ is about 35° C. to about 200° C.

23. The process of claim 22 wherein the $T_g$ is greater than about 45° C.

24. The process of claim 23, wherein the $T_g$ is greater than about 55° C.

25. The process of claim 14, wherein $T_s$ is about 2° C. to about 30° C. and $T_g$ is about 22° C. to about 200° C.

26. The process of claim 14, wherein the glassy matrix comprises a glass former chosen from the group consisting of carbohydrates, carbohydrate derivatives, carbohydrate polymers, organic carboxylic salts, synthetic organic polymers, proteins, peptides, amino acids and polyamino acids.

27. The process of claim 26, wherein the glass former is selected from the group consisting of sodium citrate, raffinose, lactose, trehalose, maltotriose, maltodextrin, maltose, glucopyranosyl-sorbitol, glucopyranosyl-mannitol, polydextrose, sucrose, cyclodextrin, casein, HSA, hydroxyethyl starch, stachyose, magnesium gluconate, and cellubiose.

28. The process of claim 14, wherein said aerosolizing step comprises aerosolizing said composition in a current of air.

29. An aerosolized powdered, dispersible composition having stable aerosol performance over time, which composition comprises:

(a) a first, respirable powdered component comprising the composition of claim 1, and (b) a second, non-respirable powdered component comprising a powdered, pharmaceutically-acceptable carrier.

30. The composition of claim 29, wherein the difference between $T_g$ and $T_s$ of that first component is at least about 20° C.

31. The composition of claim 30, wherein the difference between $T_g$ and $T_s$ is at least about 30° C.

32. The composition of claim 29, wherein the largest particle size of the first component is about 10 microns, with the majority of the particles between about 1 micron to about 5 microns, and the particle size of the second component is between about 15 microns to about 100 microns.

* * * * *